(12) United States Patent
Mazo

(10) Patent No.: US 10,580,131 B2
(45) Date of Patent: Mar. 3, 2020

(54) CONVOLUTIONAL NEURAL NETWORK FOR SEGMENTATION OF MEDICAL ANATOMICAL IMAGES

(71) Applicant: Zebra Medical Vision Ltd., Shefayim (IL)

(72) Inventor: Victoria Mazo, Hod-HaSharon (IL)

(73) Assignee: Zebra Medical Vision Ltd., Shefayim (IL)

( * ) Notice: Subject to any disclaimer, the term of this patent is extended or adjusted under 35 U.S.C. 154(b) by 123 days.

(21) Appl. No.: 15/893,636

(22) Filed: Feb. 11, 2018

(65) Prior Publication Data
US 2018/0240235 A1    Aug. 23, 2018

Related U.S. Application Data

(60) Provisional application No. 62/462,395, filed on Feb. 23, 2017.

(51) Int. Cl.
*G06K 9/00* (2006.01)
*G06T 7/00* (2017.01)
(Continued)

(52) U.S. Cl.
CPC ............. *G06T 7/0012* (2013.01); *G06N 3/04* (2013.01); *G06N 3/0454* (2013.01); *G06N 3/08* (2013.01);
(Continued)

(58) Field of Classification Search
CPC . G06T 7/0012; G06T 7/10; G06T 7/11; G06T 7/12; G06T 7/13; G06T 7/143;
(Continued)

(56) References Cited

U.S. PATENT DOCUMENTS

| 5,868,708 A | 2/1999 | Hart et al. |
|---|---|---|
| 6,962,576 B2 | 11/2005 | Sibbitt |

(Continued)

FOREIGN PATENT DOCUMENTS

| DE | 3328530 | 2/1985 |
|---|---|---|
| GB | 526145 | 9/1940 |

(Continued)

OTHER PUBLICATIONS

Communication Relating to the Results of the Partial International Search dated Feb. 4, 2015 From the International Searching Authority Re. Application No. PCT/IL2014/050863.
(Continued)

*Primary Examiner* — Jose L Couso

(57) ABSTRACT

There is provided a method for segmentation of an image of a target patient, comprising: providing a target 2D slice and nearest neighbor 2D slice(s) of a 3D anatomical image, and computing, by a trained multi-slice fully convolutional neural network (multi-slice FCN), a segmentation region including a defined intra-body anatomical feature that extends spatially across the target 2D slice and the nearest neighbor 2D slice(s), wherein the target 2D slice and each of the nearest neighbor 2D slice(s) are processed by a corresponding contracting component of sequential contracting components of the multi-slice FCN according to the order of the target 2D slice and the nearest neighbor 2D slice(s) based on the sequence of 2D slices extracted from the 3D anatomical image, wherein outputs of the sequential contracting components are combined and processed by a single expanding component that outputs a segmentation mask for the target 2D slice.

21 Claims, 6 Drawing Sheets

(51) Int. Cl.
| | |
|---|---|
| *G06N 3/04* | (2006.01) |
| *G06N 3/08* | (2006.01) |
| *G06T 7/11* | (2017.01) |
| *G16H 30/40* | (2018.01) |
| *G16H 50/50* | (2018.01) |

(52) U.S. Cl.
CPC .............. G06T 7/11 (2017.01); G16H 30/40 (2018.01); G16H 50/50 (2018.01); *G06T 2200/04* (2013.01); *G06T 2207/10081* (2013.01); *G06T 2207/10084* (2013.01)

(58) Field of Classification Search
CPC ....... G06T 7/174; G06T 7/194; G06T 3/4046; G06T 11/008; G06T 11/003; G06T 17/20; G06T 2200/04; G06T 2207/20084; G06T 2207/10072; G06T 2207/10081; G06T 2207/20081; G06T 2207/10012; G06T 2207/30004; G06T 2207/30028; G06T 2207/30081; G06T 2207/10084; G06T 2207/20221; G06T 2207/30012; G06T 2207/30096; G06T 2207/10088; G06T 2207/10136; G06T 2207/20104; G06T 2207/30068; G06T 2207/10108; G06T 2207/10132; G06T 2207/10116; G06T 2207/20076; G06T 2207/20108; G06T 2207/30048; G06T 2207/30061; G06T 2207/30101; G06T 2210/41; G06N 3/04; G06N 3/08; G06N 3/0454; G06N 3/084; G06N 3/02; G06N 3/0427; G06N 3/0472; G06N 3/086; G06N 7/046; G06N 7/005; G06N 20/00; G16H 50/50; G16H 50/20; G16H 50/30; G16H 30/40; A61B 2090/3762; A61B 6/032; A61B 6/5229; A61B 6/5258; A61B 5/7425; A61B 2034/107; A61N 5/103; A61N 5/1039; G06K 9/66; G06K 9/2054; G06K 9/3233; G06K 9/6269; G06K 9/6282; G06K 9/6267; G06K 2209/051; G06K 2209/055; G06K 2209/05; G06K 2209/053; Y10S 128/92; Y10S 128/922; Y10S 128/924; Y10S 128/925; G06F 19/321; G06F 19/3418
See application file for complete search history.

(56) References Cited

U.S. PATENT DOCUMENTS

| | | | |
|---|---|---|---|
| 10,346,986 B2 * | 7/2019 | Xu | G06N 3/0454 |
| 2001/0009989 A1 | 7/2001 | Sibbitt | |
| 2002/0010418 A1 | 1/2002 | Lary et al. | |
| 2002/0010487 A1 | 1/2002 | Evans et al. | |
| 2003/0069549 A1 | 4/2003 | MacMahon et al. | |
| 2003/0097114 A1 | 5/2003 | Ouriel et al. | |
| 2004/0004521 A1 | 1/2004 | Hasegawa | |
| 2006/0184130 A1 | 8/2006 | Sibbitt, Jr. et al. | |
| 2010/0042117 A1 | 2/2010 | Kim et al. | |
| 2011/0152683 A1 | 6/2011 | Gerrans et al. | |
| 2012/0090620 A1 | 4/2012 | Deutsch | |
| 2013/0261538 A1 | 10/2013 | Miyazaki et al. | |
| 2016/0242790 A1 | 8/2016 | Brandeis | |
| 2016/0250143 A1 | 9/2016 | Brandeis | |
| 2016/0263319 A1 | 9/2016 | Brandeis | |
| 2018/0061058 A1 * | 3/2018 | Xu | G06K 9/6269 |
| 2018/0061059 A1 * | 3/2018 | Xu | G06N 3/0454 |
| 2018/0108139 A1 * | 4/2018 | Abramoff | G06T 7/11 |
| 2018/0116620 A1 * | 5/2018 | Chen | A61B 6/03 |
| 2018/0218497 A1 * | 8/2018 | Golden | G06T 7/10 |
| 2018/0218502 A1 * | 8/2018 | Golden | G06T 7/10 |
| 2019/0201106 A1 * | 7/2019 | Siemionow | A61B 5/055 |
| 2019/0209116 A1 * | 7/2019 | Sjostrand | A61B 6/037 |
| 2019/0216409 A1 * | 7/2019 | Zhou | A61B 6/032 |
| 2019/0236782 A1 * | 8/2019 | Amit | G16H 30/20 |
| 2019/0304092 A1 * | 10/2019 | Akselrod-Ballin | G06N 3/08 |
| 2019/0340752 A1 * | 11/2019 | Brestel | G16H 40/20 |
| 2019/0340753 A1 * | 11/2019 | Brestel | G06N 3/084 |
| 2019/0340763 A1 * | 11/2019 | Laserson | G06K 9/6256 |

FOREIGN PATENT DOCUMENTS

| | | |
|---|---|---|
| WO | WO 2004/112569 | 12/2004 |
| WO | WO 2007/114934 | 10/2007 |
| WO | WO 2009/104189 | 8/2009 |
| WO | WO 2009/109967 | 9/2009 |
| WO | WO 2009/120432 | 10/2009 |
| WO | WO 2015/052702 | 4/2015 |
| WO | WO 2015/052703 | 4/2015 |
| WO | WO 2015/052704 | 4/2015 |

OTHER PUBLICATIONS

International Preliminary Report on Patentability dated Apr. 28, 2016 From the International Bureau of WIPO Re. Application No. PCT/IL2014/050862.
International Preliminary Report on Patentability dated Apr. 28, 2016 From the International Bureau of WIPO Re. Application No. PCT/IL2014/050863.
International Preliminary Report on Patentability dated Apr. 28, 2016 From the International Bureau of WIPO Re. Application No. PCT/IL2014/050864.
International Search Report and the Written Opinion dated Feb. 10, 2015 From the International Searching Authority Re. Application No. PCT/IL2014/050862.
International Search Report and the Written Opinion dated Feb. 23, 2015 From the International Searching Authority Re. Application No. PCT/IL2014/050863.
International Search Report and the Written Opinion dated Feb. 23, 2015 From the International Searching Authority Re. Application No. PCT/IL2014/050864.
Eckmann "Polidocanol for Endavenous Microfoam Sclerosant Therapy", Expert Opinion on Investigational Drugs, 18(2): 1919-1927, Dec. 2009.
Elias et al. "Mechanochemical Tumescentless Endovenous Ablation: Final Results of the Initial Clinical Trial", Phlebology, 27: 67-72, 2012.
Jones et al. "Management of Varicose Veins", American Family Physicians, 78(11): 1289-1294, 2008.
Subramonia et al. "The Treatment of Varicose Veins", Annals of The Royal College of Surgeons of England, 89(2): 96-100, Mar. 2007.

* cited by examiner

CONVOLUTIONAL NEURAL NETWORK FOR SEGMENTATION OF MEDICAL ANATOMICAL IMAGES

RELATED APPLICATION

This application claims the benefit of priority under 35 USC § 119(e) of U.S. Provisional Patent Application No. 62/462,395, filed on Feb. 23, 2017, the contents of which are incorporated herein by reference in their entirety.

BACKGROUND

The present invention, in some embodiments thereof, relates to medical anatomical images and, more specifically, but not exclusively, to a convolutional neural network for segmentation of at least one anatomical feature in medical anatomical images.

Manual visual assessment (e.g., by a radiologist) of medical anatomical images (e.g., CT, MRI, ultrasound, each of different parts of the body, for example, chest) for identification of abnormal anatomical features is a challenging and time consuming task due to the large amount of information that needs to be processed. For example, for a 3D CT and/or MRI image, a radiologist examines dozens or hundreds of 2D slices.

SUMMARY

According to a first aspect, a computer implemented method for automatic segmentation of a target two dimensional (2D) slice of a three dimensional (3D) anatomical image of a target patient and for computation of an indication of a defined intra-body anatomical feature, comprises: providing the target 2D slice of the 3D anatomical image of a target individual captured by a medical imaging modality device, and at least one nearest neighbor 2D slice of the 3D anatomical image sequentially adjacent to the target 2D slice, wherein the at least one nearest neighbor 2D slice and the target 2D slice are obtained from a sequence of 2D slices extracted from the 3D anatomical image, computing a segmentation region including a defined intra-body anatomical feature that extends spatially across the target 2D slice and the at least one nearest neighbor 2D slice, the segmentation region computed for the target 2D slices by a trained multi-slice fully convolutional neural network (multi-slice FCN) that receives the target 2D slice and the at least one nearest neighbor 2D slice as input, wherein the target 2D slice and each of the at least one nearest neighbor 2D slices are processed by a corresponding contracting component of a plurality of sequential contracting components of the multi-slice FCN according to the order of the target 2D slice and the at least one nearest neighbor 2D slice based on the sequence of 2D slices extracted from the 3D anatomical image, wherein outputs of the plurality of sequential contracting components are combined and processed by a single expanding component that outputs a segmentation mask for the target 2D slice, and providing an indication of the segmented region including the predefined intra-body anatomical feature for the target 2D slice for presentation on a display.

According to a second aspect, a computer implemented method for training a multi-slice FCN for automatic segmentation of a three dimensional (3D) anatomical image of a target patient and for computation of an indication of a defined intra-body anatomical feature, comprises: providing, for each of a plurality of respective sample individuals, a sample 2D slice of a 3D anatomical image of the respective sample individual captured by a medical imaging modality device, and at least one nearest neighbor 2D slice of the 3D anatomical image sequentially adjacent to the sample 2D slice, wherein the at least one nearest neighbor 2D slice and the sample 2D slice are obtained from a sequence of 2D slices extracted from the 3D anatomical image, wherein the sample 2D slice and the at least one nearest neighbor 2D slice each include a respective manual segmentation region denoting a defined intra-body anatomical feature that extends spatially across the sample 2D slice and the at least one nearest neighbor 2D slice, training a multi-slice FCN according to the sample 2D slice and the at least one nearest neighbor 2D slice each including the respective manual segmentation region received for each of the plurality of sample individuals, wherein the sample 2D slice and each of the at least one nearest neighbor 2D slices for each of the plurality of sample individuals are processed by a corresponding contracting component of a plurality of sequential contracting components of the multi-slice FCN according to the order of the sample 2D slice and the at least one nearest neighbor 2D slice based on the sequence of 2D slices extracted from the 3D anatomical image of the respective sample individual, wherein outputs of the plurality of sequential contracting components are combined and processed by a single expanding component that outputs a segmentation mask for the sample 2D slices, and providing the trained multi-slice FCN for computing an indication of a segmented region including a predefined intra-body anatomical feature for an input of a target 2D slice and at least one nearest neighbor 2D slice of a target individual.

According to a third aspect, a system for automatic segmentation of a target two dimensional (2D) slice of a three dimensional (3D) anatomical image of a target patient and for computation of an indication of a defined intra-body anatomical feature, comprises: a non-transitory memory having stored thereon a code for execution by at least one hardware processor of a computing device, the code comprising: code for obtaining the target 2D slice of the 3D anatomical image of a target individual captured by a medical imaging modality device, and at least one nearest neighbor 2D slice of the 3D anatomical image sequentially adjacent to the target 2D slice, wherein the at least one nearest neighbor 2D slice and the target 2D slice are obtained from a sequence of 2D slices extracted from the 3D anatomical image, code for computing a segmentation region including a defined intra-body anatomical feature that extends spatially across the target 2D slice and the at least one nearest neighbor 2D slice, the segmentation region computed for the target 2D slices by a trained multi-slice fully convolutional neural network (multi-slice FCN) that receives the target 2D slice and the at least one nearest neighbor 2D slice as input, wherein the target 2D slice and each of the at least one nearest neighbor 2D slices are processed by a corresponding contracting component of a plurality of sequential contracting components of the multi-slice FCN according to the order of the target 2D slice and the at least one nearest neighbor 2D slice based on the sequence of 2D slices extracted from the 3D anatomical image, wherein outputs of the plurality of sequential contracting components are combined and processed by a single expanding component that outputs a segmentation mask for the target 2D slice, and code for providing an indication of the segmented region including the predefined intra-body anatomical feature for the target 2D slice for presentation on a display.

The systems, methods, apparatus, and/or code instructions described herein relate to the technical problem of segmenting one or more predefined features in a 3D anatomical image. The technical problem may relate to segmenting one or more predefined features in a 2D slice of a 3D anatomical image, where the predefined feature(s) extend along two or more 2D slices of the 3D anatomical image, for example, an indication of bronchiectasis computed based on a relationship between diameters of bronchi and nearby arteries, ground glass opacity in tissue, and calcification in blood vessels (e.g., coronary arteries). For example, a nodule may appear in one 2D slice but not in nearest neighbor 2D slices, and may be a false positive result (e.g., mistaken for a blood vessel or other feature that extends across multiple nearest neighbor 2D slices).

The systems, methods, apparatus, and/or code instructions described herein improve performance of a computing device that executes the trained multi-slice FCN for automatically segmenting one or more predefined anatomical features of a 2D slice of a 3D anatomical image. The improvement in performance may be based on an increase in accuracy, sensitivity, specificity, and/or Dice score, of segmenting the predefined anatomical feature(s), for example, as described in additional detail in the Examples section.

The systems, methods, apparatus, and/or code instructions described herein improve performance of an imaging machine that captures medical images, by reducing the utilization of the imaging machine. For imaging machines that operate by emitting radiation (e.g., x-rays), the amount of emitted radiation and radiation exposure by the patient is reduced. The segmentation of the 2D slice may be performed for previously captured anatomical images, which may have been acquired for other clinical indications, acquired using a variety of imaging protocols which are not necessarily optimized for computation of the segmentation by the multi-slice FCN, and/or that are not optimized for a human reader but are able to be segmented and generate results for the human reader by the multi-slice FCN. The segmentation to identify the predefined anatomical features may be performed as an additional analysis, without necessarily requiring a dedicated image captured for optimal processing by the multi-slice FCN. For example, bronchiectasis may be automatically segmented for a cardiac CT and/or chest-abdominal CT, and calcifications in the coronary arteries may be automatically segmented on a CT scan captured for a lung indication for example CT scans performed to screen for lung cancer. It is noted that some cardiac CTs capture image around the heart and do not capture the entire lungs, however, the cardiac CT may be processed by the multi-slice FCN when the cardiac CT includes a series (i.e., a volume) that captures larger portions of the chest or the entire chest.

In a further implementation form of the first, second, and third aspects, the medical imaging modality device comprises a computer tomography (CT) device, and wherein the 2D target slice and the at least one nearest neighbor 2D slice comprise 2D axial slices of the 3D anatomical image.

In a further implementation form of the first, second, and third aspects, the defined intra-body anatomical feature comprises at least one arteriole indicative of bronchiectasis of at least one lung of the target patient.

In a further implementation form of the first, second, and third aspects, the defined intra-body anatomical feature comprises ground glass opacity (GGO) of at least one lung of the target patient.

In a further implementation form of the first, second, and third aspects, the 3D anatomical image comprises a non-cardiac non-contrast chest CT scan, and the defined intra-body anatomical feature comprises an indication of coronary calcification.

In a further implementation form of the first, second, and third aspects, the methods and/or system further comprise computing an Agatston score by multiplying an area of coronary calcification according to the segmentation region that comprises the indication of coronary calcification by a density in Hounsfield units of pixels of the segmentation region.

In a further implementation form of the first, second, and third aspects, outputs of each of the plurality of sequential contracting components comprise a respective feature map of a plurality of feature maps computed by respective sequential contracting components for respective inputs of the target 2D slice and the at least one nearest neighbor 2D slice.

In a further implementation form of the first, second, and third aspects, the plurality of feature maps outputted by the plurality of sequential contracting components are flattened into a single feature map that is fed into the single expanding component.

In a further implementation form of the first, second, and third aspects, outputs of the plurality of sequential contracting components are fed into a bidirectional gated recurrent unit (GRU), and a plurality of outputs of the bidirectional GRU are combined and processed by the single expanding component.

In a further implementation form of the first, second, and third aspects, dimensions of layers of the bidirectional GRU equal common dimensions of the target 2D slice and the at least one nearest neighbor 2D slices.

In a further implementation form of the first, second, and third aspects, outputs of a forward direction and a backward direction of the bidirectional GRU are concatenated and reshaped into dimensions corresponding to dimensions of feature map outputs of the plurality of sequential contracting components.

In a further implementation form of the first, second, and third aspects, the multi-slice FCN includes a plurality of skip connections between a certain contracting component of the plurality of sequential contracting components processing the target 2D slice and the single expanding component.

In a further implementation form of the first, second, and third aspects, at least one skip connection between at least one contracting component of the plurality of sequential contracting components processing the at least one nearest neighbor 2D slice and the single expanding component is absent from the multi-slice FCN.

In a further implementation form of the first, second, and third aspects, the target 2D slice is located within the middle of a sequence of the at least one nearest neighbor 2D slice.

In a further implementation form of the first, second, and third aspects, the at least one nearest neighbor 2D slice includes an even number of nearest neighbor 2D slices, with a first half of the even number of nearest neighbor 2D slices located sequentially prior to the target 2D slice and a second half of the even number of nearest neighbor 2D slices located sequentially after the target 2D slice.

In a further implementation form of the first, second, and third aspects, the multi-slice FCN is trained end-to-end.

In a further implementation form of the first, second, and third aspects, the sample 2D slice and the at least one nearest neighbor 2D slice of the plurality of sample individuals are raw data images extracted from the 3D anatomical image, without preprocessing.

In a further implementation form of the first, second, and third aspects, the sample 2D slice and the at least one nearest neighbor 2D slice of the plurality of sample individuals include regions where no manual segmentation is performed.

In a further implementation form of the first, second, and third aspects, the 3D anatomical images of the plurality of sample individuals include a variation of image acquisition protocols.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
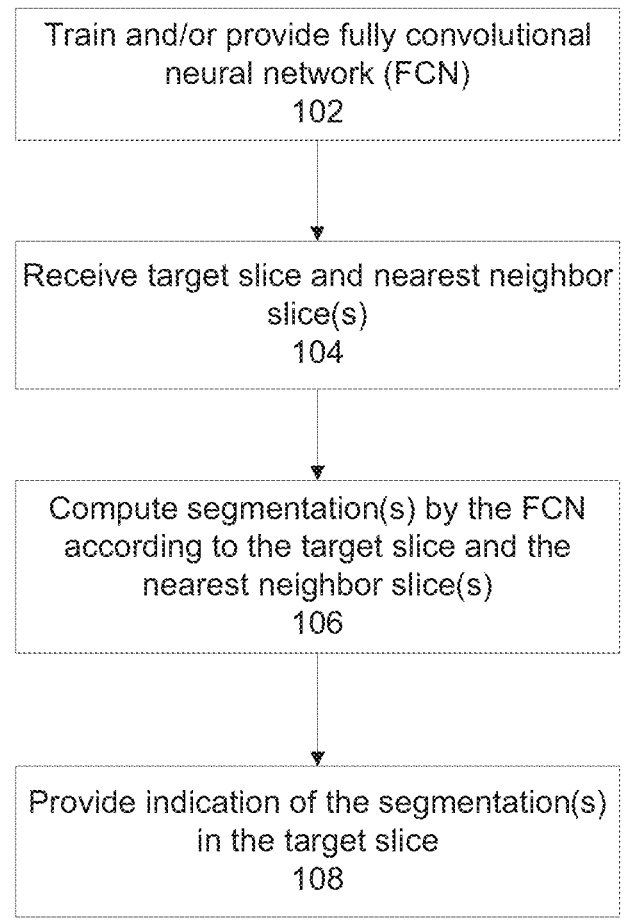
FIG. 1 is a flowchart of a method of segmenting a target 2D slice of a 3D anatomical image according to one or more nearest neighbor 2D slices, by a trained multi-slice FCN, in accordance with some embodiments of the present invention.

The present invention, in some embodiments thereof, relates to medical anatomical images and, more specifically, but not exclusively, to a convolutional neural network for segmentation of at least one anatomical feature in medical anatomical images.

An aspect of some embodiments of the present invention relates to systems, an apparatus, methods, and/or code instructions (stored in a data storage device, executable by one or more hardware processors) for automatic segmentation of a target two dimensional (2D) slice of a three dimensional (3D) anatomical image of a target patient, according to at least one nearest neighbor 2D slice of the target 2D slice. The nearest neighbor 2D slice(s) are obtained from a sequence of 2D slices extracted from the 3D anatomical image, for example, axial 2D slices of a 3D CT scan of the chest. A segmentation region is computed for the target 2D slice by a trained multi-slice fully convolutional neural network (referred to herein as multi-slice FCN) that receives the target 2D slice and the one nearest neighbor 2D slice(s) as input. The segmentation region includes a defined intra-body anatomical feature that extends spatially across the 2D slice and at least one of the nearest neighbor slices, for example, an indication of bronchiectasis (based on bronchi and arteries), an indication of ground glass opacity (GGO), and an indication of vessel calcification (e.g., coronary artery calcification). The trained multi-slice FCN includes multiple sequentially arranged contracting components, that each receive one of the target 2D or the nearest neighbor slices corresponding to the order of the target 2D and nearest neighbor slices. Outputs of the multiple sequentially arranged contracting components are combined and processed by a single expanding component that outputs a segmentation mask for the target 2D slice. The target 2D slice including the computed segmentation region(s) may be presented on a display, for example, the segmentation region(s) may be presented as colored pixels within a black and white target 2D slice.

Optionally, the outputs of the sequential contracting components are fed into a bidirectional gated recurrent unit (GRU). The outputs of the bidirectional GRU are combined and processed by the single expanding component.

Optionally, the multi-slice FCN includes skip connections between the contracting component processing the target 2D slice and the single expanding component, and excludes skip connections between the contracting component(s) processing the nearest neighbor slice(s) and the single expanding component.

An aspect of some embodiments of the present invention relates to systems, an apparatus, methods, and/or code instructions (stored in a data storage device, executable by one or more hardware processors) for training an multi-slice FCN for automatic segmentation of a target two dimensional (2D) slice of a three dimensional (3D) anatomical image of a target patient, according to at least one nearest neighbor 2D slice of the target 2D slice. The multi-slice FCN is trained according to a set of training images of multiple sample individuals, where two or more neighboring 2D slices of 3D anatomical images are manually segmented to include a defined intra-body anatomical feature that extends spatially across the two or more neighboring 2D slices. The multi-slice FCN is trained end-to-end.

Optionally, the nearest neighbor 2D training slices are raw 2D data images extracted from the 3D anatomical image, without pre-processing.

Some implementations of the systems, methods, apparatus, and/or code instructions described herein relate to the technical problem of segmenting one or more predefined features in a 3D anatomical image. The technical problem may relate to segmenting one or more predefined features in a 2D slice of a 3D anatomical image, where the predefined feature(s) extend along two or more 2D slices of the 3D anatomical image, for example, an indication of bronchiectasis computed based on a relationship between diameters of bronchi and nearby arteries, ground glass opacity in tissue, and calcification in blood vessels (e.g., coronary arteries).

For example, a nodule may appear in one 2D slice but not in nearest neighbor 2D slices, and may be a false positive result (e.g., mistaken for a blood vessel or other feature that extends across multiple nearest neighbor 2D slices).

Some implementations of the systems, methods, apparatus, and/or code instructions described herein improve performance of a computing device that executes the trained multi-slice FCN for automatically segmenting one or more predefined anatomical features of a 2D slice of a 3D anatomical image. The improvement in performance may be based on an increase in accuracy, sensitivity, specificity, and/or Dice score, of segmenting the predefined anatomical feature(s), for example, as described in additional detail in the Examples section.

Some implementations of the systems, methods, apparatus, and/or code instructions described herein improve performance of an imaging machine that captures medical images, by reducing the utilization of the imaging machine. For imaging machines that operate by emitting radiation (e.g., x-rays), the amount of emitted radiation and radiation exposure by the patient is reduced. The segmentation of the 2D slice may be performed for previously captured anatomical images, which may have been acquired for other clinical indications, acquired using a variety of imaging protocols which are not necessarily optimized for computation of the segmentation by the multi-slice FCN, and/or that are not optimized for a human reader but are able to be segmented and generate results for the human reader by the multi-slice FCN. The segmentation to identify the predefined anatomical features may be performed as an additional analysis, without necessarily requiring a dedicated image captured for optimal processing by the multi-slice FCN. For example, bronchiectasis may be automatically segmented for a cardiac CT and/or chest-abdominal CT, and calcifications in the coronary arteries may be automatically segmented on a CT scan captured for a lung indication for example CT scans performed to screen for lung cancer. It is noted that some cardiac CTs capture image around the heart and do not capture the entire lungs, however, the cardiac CT may be processed by the multi-slice FCN when the cardiac CT includes a series (i.e., a volume) that captures larger portions of the chest or the entire chest.

Some implementations of the systems, methods, apparatus, and/or code instructions described herein improve an underling technical process within the technical field of medical image processing by a trained convolutional neural network, in particular, within the field of automatic segmentation of 2D image slices to identify one or more predefined anatomical features.

Some implementations of the systems, methods, apparatus, and/or code instructions described herein provide a unique, particular, and advanced architecture of a multi-slice FCN that segments a target 2D slice of a 3D anatomical image to identify at least one predefined anatomical feature, by processing one or more nearest neighbors 2D slices of the target 2D slice.

Some implementations of the systems, methods, apparatus, and/or code instructions described herein do not simply perform automation of a manual procedure, but perform additional automated features which cannot be performed manually by a human using pencil and/or paper. For example, the multi-slice FCN learns which features to automatically extract from the 2D target slice and the nearest neighbor 2D slice(s) to automatically compute the segmentation regions. The automatically extracted features are unlike any features a human interpreter relies on. Moreover, no handcrafted features are necessarily required, since features are automatically learned and extracted by the multi-slice FCN.

Some implementations of the systems, methods, apparatus, and/or code instructions described herein generate new data in the form of the trained multi-slice FCN that processes the target 2D slice and one or more nearest neighbors 2D slices of the target 2D slice, and/or generates new data in the form of the outputted target 2D slice that includes an annotation of the segmented region(s).

Some implementations of the systems, methods, apparatus, and/or code instructions described herein are tied to physical real-life components, for example, the imaging machine that generates the 2D slices and/or the 3D image from which the 2D slices are extracted, computational hardware (e.g., hardware processors, physical data storage devices) that analyze the 2D image slices, and a display that presents the target 2D slice with annotated segmented region(s).

Accordingly, some implementations of the systems, methods, apparatus, and/or code instructions described herein are inextricably tied to computer technology and/or physical components (e.g., imaging machine, hardware processor(s), data storage device(s), display) to overcome an actual technical problem arising in segmenting 2D anatomical image slices.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the terms target 2D slice and target slice may sometimes be interchanged. As used herein, the terms nearest neighbor 2D slice and nearest neighbor slice may sometimes be interchanged.

Examples of applications of segmentation by the multi-slice FCN include an indication of one or more of the following within the segmented region: bronchiectasis, ground glass, and coronary calcification.

In some implementations, the systems, methods, apparatus, and/or code instructions described herein address the technical problem of identification of an indication of bronchiectasis in a 2D anatomical slice optionally acquired by a CT machine. In some implementations, the systems, methods, apparatus, and/or code instructions described herein include and/or train a multi-slice FCN for segmenting a 2D anatomical slice (optionally acquired by a CT machine) to include an indication of bronchiectasis.

Bronchiectasis is a Chronic Obstructive Pulmonary Disease (COPD), which is the number one cause of hospital admission in Canada. Bronchiectasis is defined to be localized and irreversible dilation of bronchial walls and is traditionally diagnosed using computed tomography (CT). In normal subjects, the diameter of the bronchi and the closeby pulmonary arteries are similar, and the bronchoarterial ratio (i.e., ratio of the diameter of the bronci divided by the diameter of the nearby pulmonary artery) is around 0.65-0.70. When the bronchoarterial ratio is greater than 1, bronchiectasis may be diagnosed. Bronchiectasis is caused by a prolonged vicious cycle of airway inflammation and the altered response to infection, for example, as described with reference to Moulton, B. C. and Barker, A. F. *Pathogenesis of bronchiectasis. Clinics in Chest Medicine,* 33:211-217, 2012. It has recently been demonstrated that patients with bronchiectasis have a progressive decline in lung function, for example, as described with reference to King, P. T. *The pathophysiology of bronchiectasis. International Journal of Chronic Obstructive Pulmonary Disease,* 4:411-419, 2009, and thus manages as a debilitating illness that is responsible for significant morbidity with a substantial socioeconomic burden, for example, as described with reference to Wang, Z. L. *Bronchiectasis: Still a problem. Chinese Medical Journal.,* 127:157-172, 2014 with increasing mortality rate attributed to its increased recognition, for example, as described with reference to Soyza, A. De, Brown, J. S., and Loebinger, M. R. *Research priorities in bronchiectasis. Thorax,* 68(7):695-696, 2013. It is estimated that annually over 110,000 patients in the United States are receiving treatment for bronchiectasis related morbidity, with an annual medical-care expenditures of $630 million, for example, as described with reference to Weycker, D., Edelsberg, J., Oster, G., and Tino, G. *Prevalence and economic burden of bronchiectasis. Clinical Pulmonary Medicine,* 12(4):205-209, 2005. In England and Wales 5745 bronchiectasis related deaths were registered in the period between 2001 and 2007 with statistical analyses suggesting that the mortality rate is currently increasing at 3%/year, for example, as described with reference to Roberts, H. J. and Hubbard, R. *Trends in bronchiectasis mortality in england and wales. Respiratory Medicine,* 104(7):981-985, 2010. Bronchiectasis related morbidities include, for example, increased arterial stiffness (which in turn increase the morbidity and mortality risk of a cardiovascular cause), increased inflammation, reduced exercise capacity, and bone thinning which further requires medical evaluation, surveillance and proper treatment, for example, as described with reference to Gale, N. S., Bolton, C. E., Duckers, J. M., Enright, S., Cockcroft, J. R., and Shale, D. J. *Systemic comorbidities in bronchiectasis. Chronic Respiratory Disease,* 9 (4):231-238, 2012. An important co-morbidity is COPD, for example, as described with reference to Hurst, J. R., Elborn, J. S., Soyza, A. De, Bilton, D., Bradley, J., Brown, J. S., and Winstanley, C. *Copd-bronchiectasis overlap syndrome. European Respiratory Journal.,* 45 (3):310-313, 2015. In particular, moderate to severe COPD where there is a high prevalence of bronchiectasis, for example, as described with reference to Martinez-Garcia, M. A., Soler-Cataluna, J. J., Sanz, E D., Serra, P. C., Lerma, M. A., Vicente, J. B., and Perpia-Tordera, M. *Factors associated with bronchiectasis in patients with copd. Chest,* 140(5): 1130-1137, 2011 (that were found to be an independent risk factor for all-cause mortality in COPD patients, for example, as described with reference to Mao, B., Lu, H. W., Li, M. H., Fan, L. C., Yang, J. W., Miao, X. Y, and Xu, J. F. *The existence of bronchiectasis predicts worse prognosis in patients with copd. Scientific Reports,* 5:10961, 2015 and play a major role as a prognostic factor and the usage of proper treatment options as targeted therapies, for example, as described with reference to Rademacher, J. and Welte, T. *Bronchiectasis—diagnosis and treatment. Deutsches rzteblatt International,* 108(48):809-815, 2011. Novosad, S. A. and Barker, A. F. *Chronic obstructive pulmonary disease and bronchiectasis. Current Opinion in Pulmonary Medicine,* 19(2):133-139, 2013.

It is noted that previously described computed based automated methods for detection of bronchiectasis are unsatisfactory for clinical use, and operate on methods that are different than the trained multi-slice FCN and/or the training of the multi-slice FCN described herein. For example, in the last decades two main approaches for automatic bronchiectasis detection have been developed. A first method is based on computing a tree model of the airways followed by automated measurements of broncho-arterial ratios at peripheral airway locations, for example, as described with reference to Odry, B. L., Kiraly, A. P., Novak, C. L., Naidich, D. P., and Lerallut, J.-F. *An evaluation of automated bronchoarterial ratios for reliable assessment of bronchiectasis. n Medical Imaging* 2008: *Computer-Aided Diagnosis,* volume 6915, pp. 69152M, 2008, Kiraly, P. A., Odry, B., Godoy, M. C. B., Geiger, B., Novak, C. L., and Naidich, D. *Computer-aided diagnosis of the airways: Beyond nodule detection. Journal of Thoracic Imaging,* 23(2):105-113, 2008, Yu, Nan, Li, Hua, Wu, Boyun, Li, Yan, Deng, Lei, and Guo, Youmin. *Computerized identification of bronchiectasis using a 3d quantitative ct protocol. Journal of Medical Imaging and Health Informatics,* 6(5), 2016. A second method is based on training a classifier on extracted texture and/or shape features from images to learn discriminative properties of the features for example, as described with reference to Arunkumar, R. *Quantitative analysis of bronchiectasis using local binary pattern and fuzzy based spatial proximity. International Conference on Recent Trends in Information Technology,* pp. 72-76, 2012, Elizabeth, D. Shiloah, Kannan, A., and Nehemiah, H. Khanna. *Computer aided diagnosis system for the detection of bronchiectasis in chest computed tomography images. International Journal of Imaging Systems and Technology,* 19(4):290-298, 12 2009. These methods usually use only intensity or shape features and suffer from inaccurate assumptions about the underlying morphological and other appearance characteristics of the anatomical structures. In addition, the number of samples for feature learning or CT segmentation is small and is not sufficient to reveal its intrinsic properties, which may cause overfitting and lead to low generalization ability of identification method.

In some implementations, the systems, methods, apparatus, and/or code instructions described herein address the technical problem of identification of an indication of ground glass opacity (GGO) in a 2D anatomical slice optionally acquired by a CT machine. In some implementations, the systems, methods, apparatus, and/or code instructions described herein include and/or train a multi-slice FCN for segmenting a 2D anatomical slice to include an indication of GGO.

Ground Glass Opacity (GGO) is a frequent visual finding on CT. GGO is a radiologic feature which appears as a hazy region with vague boundaries on Chest CT scans. GGO is a non-specific sign seen in various pathologies, most commonly: alveolar inflammation, infection, hemorrhage, edema or cancer. Relative to more discreet findings, GGO is often considerably more subtle and thus overlooked. It is fairly nonspecific, since any pathophysiological condition, which decreases the air content within the aerated lung parenchyma without totally obliterating the alveoli, such as alveolar inflammation, infection, hemorrhage, edema or cancer, may produce a ground-glass-like opacity. However, the presented pattern of GGO (patchy, diffuse or nodular), the general appearance of lung parenchyma (with or without fibrotic changes) and both type and duration of symptoms (acute, subacute, chronic) may aid in diagnosis, further management and treatment. The most troublesome diagnosis not to be missed is bronchioloalveolar carcinoma, for example, as described with reference to Infante, M., et al.: *Differential diagnosis and management of focal ground-glass opacities. European Respiratory Journal* 33, 821-827 (2009), which might appear as a focal GGO, with malignancy rates for persistent GGOs estimated to be 75%, for example, as described with reference to Kim, H. Y., Shim. Y. M., Lee, K. S., Han, J., Yi, C. A., Kim, Y. K.: *Persistent pulmonary nodular ground-glass opacity at thin-section CT: histopathologic comparisons. Radiology* 245, 267-275 (2007). A focal GGO with rounded, lobulated pleural indentation gives a greater than average likelihood of being malignant, for example, as described with reference to Fan, L., Liu, S. Y., Li, Q. C., Yu, H., Xiao, X. S.: *Multidetector CT features of pulmonary focal ground-glass opacity: differences between benign and malignant. Br. J. Radiology* 85, 897-904 (2012) but with a much higher probability of being cured by surgery compared to lung cancers with solid nodule appearance, for example, as described with reference to Kobayashi, Y., Mitsudomi, T.: *Management of ground-glass opacities: should all pulmonary lesions with ground-glass opacity be surgically resected? Translational Lung Cancer Research* 2(5), 354-363 (2013). GGO with increased size and high pixel attenuation suggests that it is more likely to be an invasive adenocarcinomas, for example, as described with reference to Park, C. M. Goo, J. M., Lee, H. J., Lee, C. H., Chun, E. J., Im, J. G.: *Nodular Ground-Glass Opacity at Thin-Section CT: Histologic Correlation and Evaluation of Change at Follow-up. RadioGraphics* 27(2), 391-408 (2007) and have established guidelines of proper management, for example, as described with reference to Bankier, A. A., Macmahon, H., Travis, W. D.: *Recommendations for the Management of Subsolid Pulmonary Nodules Detected at CT: A Statement from the Fleischner Society. Radiology* 266(1), 304-317 (2013). Early detection of GGOs is of great importance for early diagnosis and possible cure of lung cancers, but it is much more challenging than the currently almost-mature solid nodule detection, e.g. Ypsilantis, P. P., Montana, G.: *Recurrent Convolutional Networks for Pulmonary Nodule Detection in CT Imaging.* arXiv:1609.09143 [cs.CV] (2016), since GGO usually has an irregular shape, indistinct boundary and shares a similar intensity with the vessel attached to it.

It is noted that previously described computed based automated methods for detection of GGO are based on hand engineered features, for example, as described with reference to Linying, L. et al.: *A Review of Ground Glass Opacity Detection Methods in Lung CT Images. Current Medical Imaging Reviews* 13, 20-31 (2017). Such methods are based on intensity or shape features and suffer from inaccurate assumptions about the underlying morphological and other appearance characteristics of the anatomical structures. Moreover, the number of samples for feature learning and evaluation of a method (25-153 according to Linying et al.) is not sufficient to reveal its intrinsic properties, which may cause overfitting and lead to low generalization ability of identification method. Other attempts of GGO detection were based on CNNs, for example, as described with reference to Shin, H.-C. et al.: *Deep Convolutional Neural Networks for Computer-Aided Detection: CNN Architectures, Dataset Characteristics and Transfer Learning. IEEE Trans. Med. Imag.* 35, 1285-1298 (2016), Anthimopoulos, M., Christodoulidis, S., Ebner, L., Christe, A., Mougiakakou, S.: *Lung Pattern Classification for Interstitial Lung Diseases Using a Deep Convolutional Neural Network. IEEE Trans. Med. Imag.* 35, 1207-1216 (2016), in which the ILD dataset was used, for example, as described with reference to Depeursinge, A. et al.: *Building a reference multimedia database for interstitial lung diseases. Comput. Med. Imaging and Graph.* 36, 227-238 (2012), which contains several hundreds of slices with GGO. However, in contrast with the trained multi-slice FCN described herein that utilizes a target slice and nearest neighbor slice(s) to achieve high accuracy of segmentation, Anthimopoulos et al. performed only patch classification with a small convolutional network, while Shin et al. reported low accuracy for slice classification with GoogLeNet, at 57%.

In some implementations, the systems, methods, apparatus, and/or code instructions described herein address the technical problem of identification of an indication of coronary calcification. The technical problem may relate to identification of the indication of coronary calcification based on CT scans that are non-contrast and/or captured for non-cardiac indications (i.e., non-cardiac CT scans), for example, a chest CT scan captured according to a protocol designed to enhance the lung tissue. Such non-cardiac CT scans are captured using protocols designed to enhance tissues other than the heart. In some implementations, the systems, methods, apparatus, and/or code instructions described herein include and/or train a multi-slice FCN for segmenting a 2D anatomical slice of a non-cardiac CT scan to include an indication of coronary calcification.

Cardiovascular disease (CVD) is the leading cause of death in the United States, for example, as described with reference to *"Health, united states, 2016: With chartbook on longterm trends in health,"* 2017. The amount of coronary artery calcification (CAC) is a powerful predictor of cardiovascular events and mortality, for example, as described with reference to R Detrano, A D Guerci, J J Carr, D E Bild, G Burke, A R Folsom, K Liu, S Shea, M Szklo, D A Bluemke, D H O'Leary, R Tracy, K Watson, N D Wong, and R A Kronmal, *"Coronary calcium as a predictor of coronary events in four racial or ethnic groups,"* New England Journal of Medicine, 2008. In clinical practice, CAC is identified and quantified in terms of the Agatston score, for example, as described with reference to A S Agatston, W R Janowitz, F J Hildner, N R Zusmer, M Viamonte, and R Detrano, *"Quantification of coronary artery calcium using ultrafast computed tomography,"* American College of Cardiology, 1990, using a dedicated ECG-synchronized cardiac Calcium Scoring CT (CSCT), followed by a human operator manually identifying CAC lesions. In recent years it has been shown that the much more widely performed non-ECG-synchronized chest CT (Chest CT) provides similar diagnostic information across categories of CAC scores, for example, as described with reference to X Xie, Y Zhao, G H de Bock, P A de Jong, W P Mali, M Oudkerk, and R Vliegenthart, *"Validation and prognosis of coronary artery calcium scoring in nontriggered thoracic computed tomography: Systematic review and meta-analysis,"* Circulation: Cardiovascular Imaging, 2013. It is noted that previously described computed based automated methods for estimating coronary calcification and/or Agatson scores are from CT scans, mostly CSCT. I Isgum, M Prokop, M Niemeijer, M A Viergever, and B van Ginneken, *"Automatic coronary calcium scoring in low-dose chest computed tomography,"* TMI, 2012 relates to a method based on labeling data and training combination of KNN and SVM classifiers to automatically identify CAC in Chest CT, using both local image features and location information (based on apriory probability map). Shahzad et al. R Shahzad, T van Walsum, M Schaap, A Rossi, S Klein, A C Weustink, P J de Feyter, L J van Vliet, and W J Niessen, *"Vessel specific coronary artery calcium scoring: an automatic system,"* Academic radiology, 2013 detected CAC in CSCT scans using a KNN classifier based on local image descriptors and location features based on CCTA atlases. J M Wolterink, T Leiner, R A P Takx, M A Viergever, and I Isgum, *"Automatic coronary calcium scoring in non-contrast-enhanced ecg-triggered cardiac ct with ambiguity detection,"* TMI, 2015 extended Isgum's work for CSCT, where randomized decision trees were used for vessel specific CAC classifiers and included human-in-the-loop for ambiguous detections. N Lessmann, I Isgum, A A A Setio A A, B D de Vos, F Ciompi, P A de Jong, M Oudkerk, W P T M Mali, M A Viergever, and B van Ginneken, *"Deep convolutional neural networks for automatic coronary calcium scoring in a screening study with low-dose chest ct,"* in SPIE Medical Imaging, 2016 presented patch-based CNN segmentation approach for the identification of CAC lesions in Chest CTs, where each voxel is represented by three centered orthogonal slices and classified using three concurrent CNNs. G Santini, D Della Latta, N Martini, G Valvano, A Gori, A Ripoli, C L Susini, L Landini, and D Chiappino, "*An automatic deep learning approach for coronary artery calcium segmentation,*" in *EMBEC & NBC.* 2017 has recently presented another patch-based deep learning approach for CCS in CSCT scans.

Figure 2:
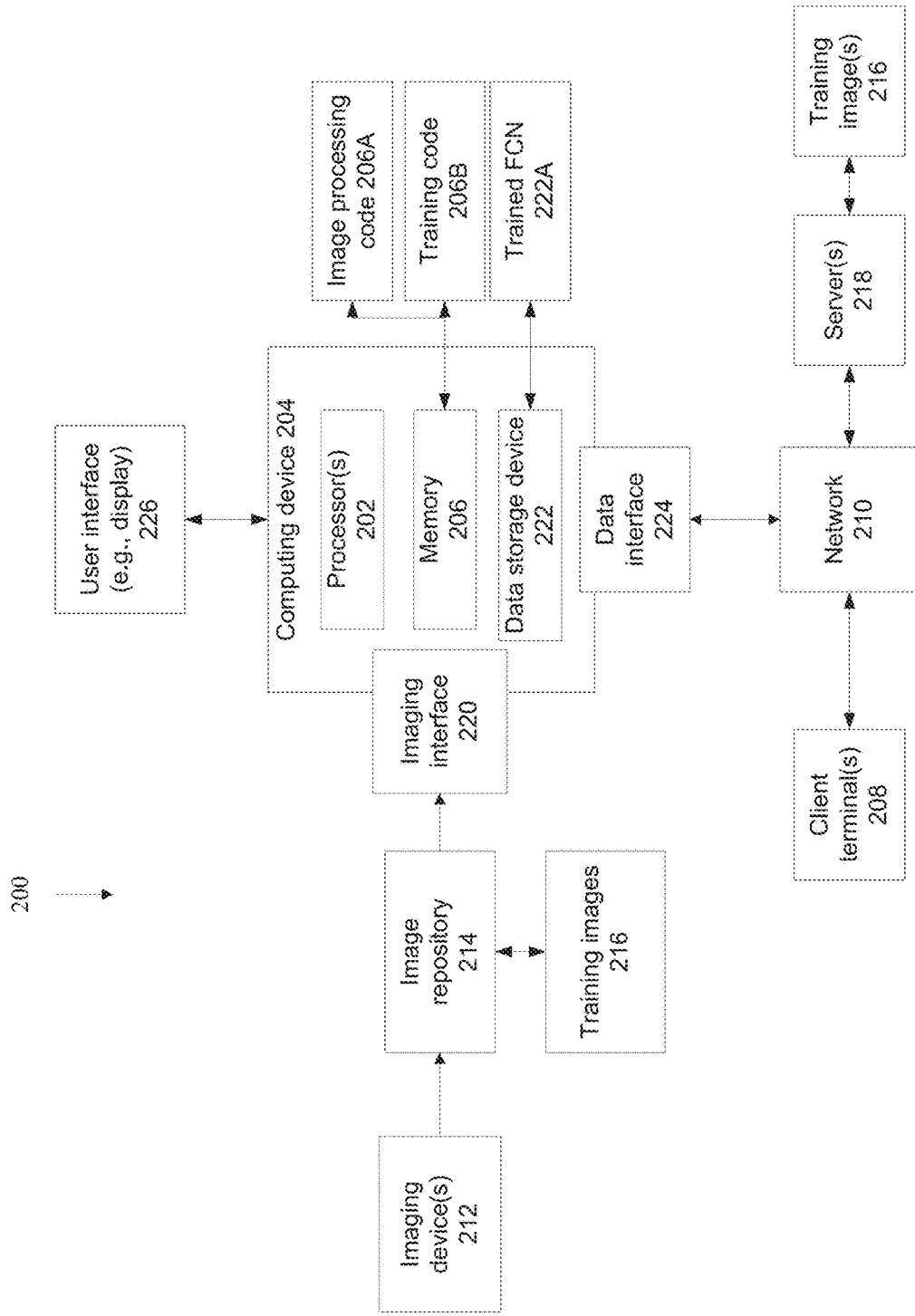
FIG. 2 is a block diagram of components of a system for segmenting a target 2D slice of a 3D anatomical image according to one or more nearest neighbor 2D slices, by a trained multi-slice FCN, and/or for training the multi-slice FCN, in accordance with some embodiments of the present invention.
Figure 3:
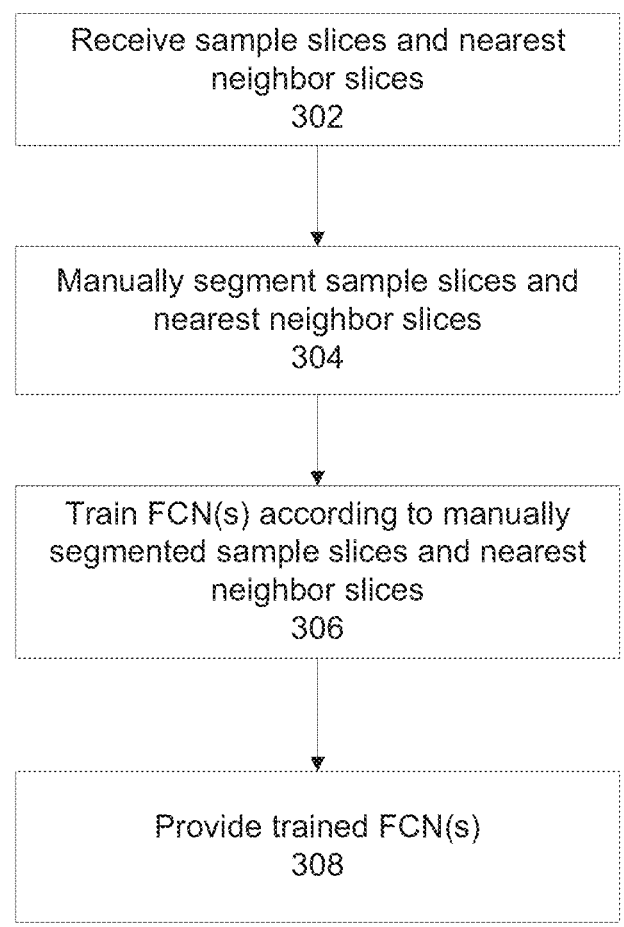
FIG. 3 is a flowchart of a method of training the multi-slice FCN, in accordance with some embodiments of the present invention.

Reference is now made to FIG. 1, which is a flowchart of a method of segmenting a target 2D slice of a 3D anatomical image according to one or more nearest neighbor 2D slices, by a trained multi-slice FCN, in accordance with some embodiments of the present invention. Reference is also made to FIG. 2, which is a block diagram of components of a system 200 for segmenting a target 2D slice of a 3D anatomical image according to one or more nearest neighbor 2D slices, by a trained multi-slice FCN, and/or for training the multi-slice FCN, in accordance with some embodiments of the present invention. Reference is also made to FIG. 3, which is a flowchart of a method of training the multi-slice FCN for segmenting a target 2D slice of a 3D anatomical image according to one or more nearest neighbor 2D slices, described with reference to FIG. 1, in accordance with some embodiments of the present invention. System 200 may implement the acts of the method described with reference to FIG. 1 and/or FIG. 3, optionally by a hardware processor(s) 202 of a computing device 204 executing code instructions stored in a data storage device 206.

The multi-slice FCN described herein is designed to learn imaging features that capture inter-slice spatial correlations to improve detection and/or segmentation of intra-body anatomical features that extend across multiple slices. For example, since most of the abnormal lung airways, lung GGO, and blood vessel calcifications extend through several slices, looking at adjacent slices above and/or below improves the ability of the multi-slice FCN to locate the anatomical feature and make a better decision whether the anatomical feature is included in the segmented region or not.

Computing device 204 may be implemented as, for example, a client terminal, a server, a radiology workstation, a virtual machine, a computing cloud, a mobile device, a desktop computer, a thin client, a Smartphone, a Tablet computer, a laptop computer, a wearable computer, glasses computer, and a watch computer. Computing 204 may include an advanced visualization workstation that sometimes is add-on to a radiology workstation and/or other devices for presenting the segmentations and/or other computer added detections to the radiologist.

Computing device 204 may include locally stored software that performs one or more of the acts described with reference to FIG. 1 and/or FIG. 3, and/or may act as one or more servers (e.g., network server, web server, a computing cloud, virtual server) that provides services (e.g., one or more of the acts described with reference to FIG. 1 and/or FIG. 3) to one or more client terminals 208 (e.g., remotely located radiology workstations, remote picture archiving and communication system (PACS) server, remote electronic medical record (EMR) server) over a network 210, for example, providing software as a service (SaaS) to the client terminal(s) 208, providing an application for local download to the client terminal(s) 208, and/or providing functions using a remote access session to the client terminals 208, such as through a web browser.

Computing device 204 receives 3D imaging data and/or a set of 2D slices (optionally extracted from 3D imaging data) captured by an imaging machine(s) 212, for example, a magnetic resonance imaging (MRI) device, a computer tomography (CT) machine, an ultrasound machine, and/or a breast tomosynthesis device. Anatomical images (i.e., the 3D data, and/or 2D slices) captured by imaging machine 212 may be stored in an image repository 214, for example, a storage server, a computing cloud, virtual memory, and a hard disk. The anatomical images stored by image repository 214 may include images of patients for analysis, and/or training images 216 that have been previously analyzed (e.g., by radiologists) and manually annotated with features of interest.

Anatomical images captured by imaging machine(s) 212 depict anatomical features and/or anatomical structures within the body of the target patient.

Training images 216 are used to train the multi-slice FCN, as described herein. It is noted that training images 216 may be stored by a server 218, accessibly by computing device 204 over network 210, for example, a publicly available training dataset, and/or a customized training dataset created for training the multi-slice FCN described herein.

Computing device 204 may receive the anatomical image(s) (i.e., 3D data, and/or set of 2D image slices) from imaging device 212 and/or image repository 214 using one or more imaging interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, program store 206 may store image processing code 206A that implement one or more acts and/or features of the method described with reference to FIG. 1, and/or training code 206B that execute one or more acts of the method described with reference to FIG. 3, and/or code instructions of trained multi-slice FCN 222A.

Computing device 204 may include a data storage device 222 for storing data, for example, a trained multi-slice FCN 222A (as described herein), training images 216, and/or electronic medical records. Data storage device 222 may be implemented as, for example, a memory, a local hard-drive, a removable storage device, an optical disk, a storage device, and/or as a remote server and/or computing cloud (e.g., accessed over network 210). It is noted that trained multi-slice FCN 222A, training images 216, and/or electronic medical records may be stored in data storage device 222, with executing portions loaded into memory 206 for execution by processor(s) 202.

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated training images 216 and/or to download an updated version of image processing code, training code, and/or the trained multi-slice FCN.

Computing device 204 may communicate using network 210 (or another communication channel, such as through a direct link (e.g., cable, wireless) and/or indirect link (e.g., via an intermediary computing device such as a server, and/or via a storage device) with one or more of:

- Client terminal(s) 208, for example, when computing device 204 acts as a server providing image analysis services (e.g., SaaS) to remote radiology terminals, for analyzing remotely obtained 3D anatomical images and/or 2D slices for detection of defined anatomical feature(s).
- Server 218, for example, implemented in association with a PACS, which may storage large numbers of 3D anatomical images and/or 2D slices for analysis, for example, captured by an imaging machine of a radiology clinic.
- Anatomical image repository 214 that stores 3D anatomical images and/or 2D slices and/or imaging device 212 that outputs the 3D images and/or 2D slices.

It is noted that imaging interface 220 and data interface 224 may exist as two independent interfaces (e.g., two network ports), as two virtual interfaces on a common physical interface (e.g., virtual networks on a common network port), and/or integrated into a single interface (e.g., network interface).

Computing device 204 includes or is in communication with a user interface 226 that includes a mechanism designed for a user to enter data (e.g., patient data) and/or view the computed segmentation. Exemplary user interfaces 226 include, for example, one or more of, a touchscreen, a display, a keyboard, a mouse, and voice activated software using speakers and microphone.

At 102, the code for the trained multi-slice FCN e.g., 220A) is provided and/or trained as described below with reference to FIG. 3.

Optionally, multiple multi-slice FCNs are trained, each for segmenting a certain anatomical feature. One or more multi-slice FCNS may be selected for segmentation of the image. For example, the user may manually select the multi-slice FCN according to the desired anatomical feature. Alternatively, all or a selected subset of multi-slice FCNs are selected (automatically and/or manually) to identify relevant anatomical features according to the imaging modality of the image and/or according to the body location captured in the image.

At 104, a target 2D slice and one or more nearest neighbor 2D slices are received for analysis by computing device 204. The target 2D slice and nearest neighbor 2D slices may be extracted from a 3D anatomical image of a target individual captured by a medical imaging modality device. For example, the medical imaging modality device may include a CT and/or MRI that captures 3D volume data. The 2D target slice and the nearest neighbor 2D slice include 2D slices of the 3D anatomical image, for example, axial 2D slices. The target 2D slice and nearest neighbor 2D slices may be independently obtained images. For example, each 2D slice may be captured by an ultrasound transducer that is adjusted to capture the 2D slices that are spatially neighboring one another, for example, by an ultrasound operator adjusting the tilt angle of the ultrasound transducer.

The target 2D slice and nearest neighbor slice(s) may overlap one another, may be adjacent to one another, and/or may be spaced apart from one another.

The nearest neighbor 2D slice(s) include 2D slices before and/or after the target 2D slice. The target 2D slice may be located within the middle of a sequence of the nearest neighbor 2D slices. When the number of nearest neighbor 2D slices is an even number a first half of the even number of nearest neighbor 2D slices may be located sequentially prior to the target 2D slice and a second half of the even number of nearest neighbor 2D slices may be located sequentially after the target 2D slice.

For example, when the target 2D slice is noted as position i within the sequence of 2D slices extracted from the 3D image, the 4 nearest neighbor slices located sequentially before and after the 2D slice are denoted as i−2, i−1, i+1, and i+2. It is noted that other number of nearest neighbor slices may be provided, for example, 1, 2, 3, 5, 6, or higher number. Alternatively, when the number of nearest neighbor 2D slices is an odd number, the target 2D slice may be located approximately in the middle of the sequence of the nearest neighbor 2D slice. For example, 3 nearest neighbor slices may be denoted as i−1, i+1, and i+2 related to the target 2D slice denoted i.

It is noted that for a 3D image from which multiple 2D slices are extracted, multiple target 2D slices may be analyzed by the trained multi-slice FCN, to cover the volume within the 3D image. For example, for a 3D image from which 10 2D slices are extracted, and when 4 nearest neighbor slices are extracted for each target slice, the first target slice analyzed is slice #3, with slices #1,2,4,5 as nearest neighbor slices. The second target slice analyzed is slice #4, with slices #2,3,5,6 as nearest neighbor slices. The last target slice analyzed is slice #8, with slices #6,7,9,10 as nearest neighbor slices. Alternatively, the target slices may be selected using manual and/or automatic methods, for example, by a radiologist to obtain an automated analysis for selected target slices, and/or by code that identifies a certain organ (e.g., heart) within the 3D image volume and selects the target slices that include the organ.

In order to analyze the edge slices (i.e., the first and/or last slices), which are missing a neighboring slice and therefore cannot be designated as the target slice, one or more of the following methods may be implemented: (i) adding blank frame(s) (e.g., all black, all white) in place of the missing neighbor slice(s), (ii) adding frame(s) with don't-care values for example pixel intensity values that do not exist in an imaging scan (e.g., negative values) in place of the missing neighbor slice(s), (iii) wrapping the slices around by designating the last slice(s) as nearest neighbor(s) of the first slice and/or designating the first slice(s) as nearest neighbor(s) of the last slice, (iv) ignoring the first one or more slices until enough slices are available as nearest neighbor slices. The one or more of methods (i)-(iv) to implement may be selected, for example, by training one FCN for each of methods (i)-(iv), and comparing the performance of the trained FCNs.

The target slice and nearest neighbor slices may be obtained from patients undergoing routine CT imaging (i.e., not selected for diagnosis of the anatomical feature within the computed segmented region), which may undergo additional automatic screening analysis, such as in a by-the-way analysis routinely performed on every (or selected) acquired medical imaging data for every (or selected) patient, to detect the presence (or probability of the presence) of the anatomical feature within the computed segmented region. For example, the target slice and nearest neighbor slices may be performed as a retrospective study on imaging studies performed in the past for other clinical indications. Conditions that have been ignored and/or overlooked in the past may be detected by the multi-slice FCN described herein. For example, the radiologist reviewing chest CTs performed for lung cancer screening may not have indicated calcifications in the coronary arteries. The additional screening may be performed without requiring additional significant radiologist reading time. There may be some additional radiologist reading time, for example, to supervise the batch output and/or evaluate particular images. The patient may not require additional specialized imaging designed to screen and/or diagnose the anatomical feature, which may expose the patient to additional radiation. Moreover, additional costs to the healthcare system are saved, and/or additional radiologist time (which is an already scare resource) is saved. The segmentation region that includes the anatomical feature does not require dedicated scan settings, and/or additional hardware. The segmentation region that includes the anatomical feature may be computed from images obtained from existing equipment, such as by installation of code implemented using processors of existing computing units to perform the methods described herein.

The anatomical image may have been ordered for a conventional clinical indication, for example, low dose anatomical imaging of the chest to screen for lung cancer, anatomical imaging to screen for colon cancer, standard non-contrast anatomical imaging of the chest, intravenous (IV) contrast anatomical imaging of the chest, standard non-contrast anatomical imaging of the abdomen, IV contrast anatomical imaging of the abdomen, oral contrast anatomical imaging of the abdomen, pelvic anatomical imaging, or other anatomical imaging study protocols. The anatomical imaging may have been ordered, for example, to help determine the cause of a bowel obstruction, to help diagnose appendicitis, assess complications of pancreatitis, screening for color cancer (i.e., virtual colonoscopy), evaluation of the urogenital system (i.e., imaging urography), pre-operative work-up, or other reasons.

At 106, the multi-slice FCN (optionally one or more selected multi-slice FCNs) receives as input the target 2D slice and the nearest neighbor 2D slices, and computes a segmentation region that includes a defined intra-body anatomical feature. The intra-body anatomical feature extends spatially across the target 2D slice and the nearest neighbor 2D slice.

For example, the defined intra-body anatomical feature within the segmented region includes arteriole(s) and/or brochi indicative of bronchiectasis within lung(s) of the target patient appearing within the target slice. In another example, the defined intra-body anatomical feature within the segmented region includes an indication of GGO within lung(s) of the target patient appearing within the target slice. In another example, the defined intra-body anatomical feature within the segmented region includes an indication of blood vessel calcification, optionally calcifications within the coronary arteries of the heart of the target patient appearing within the target slice.

Figure 4:
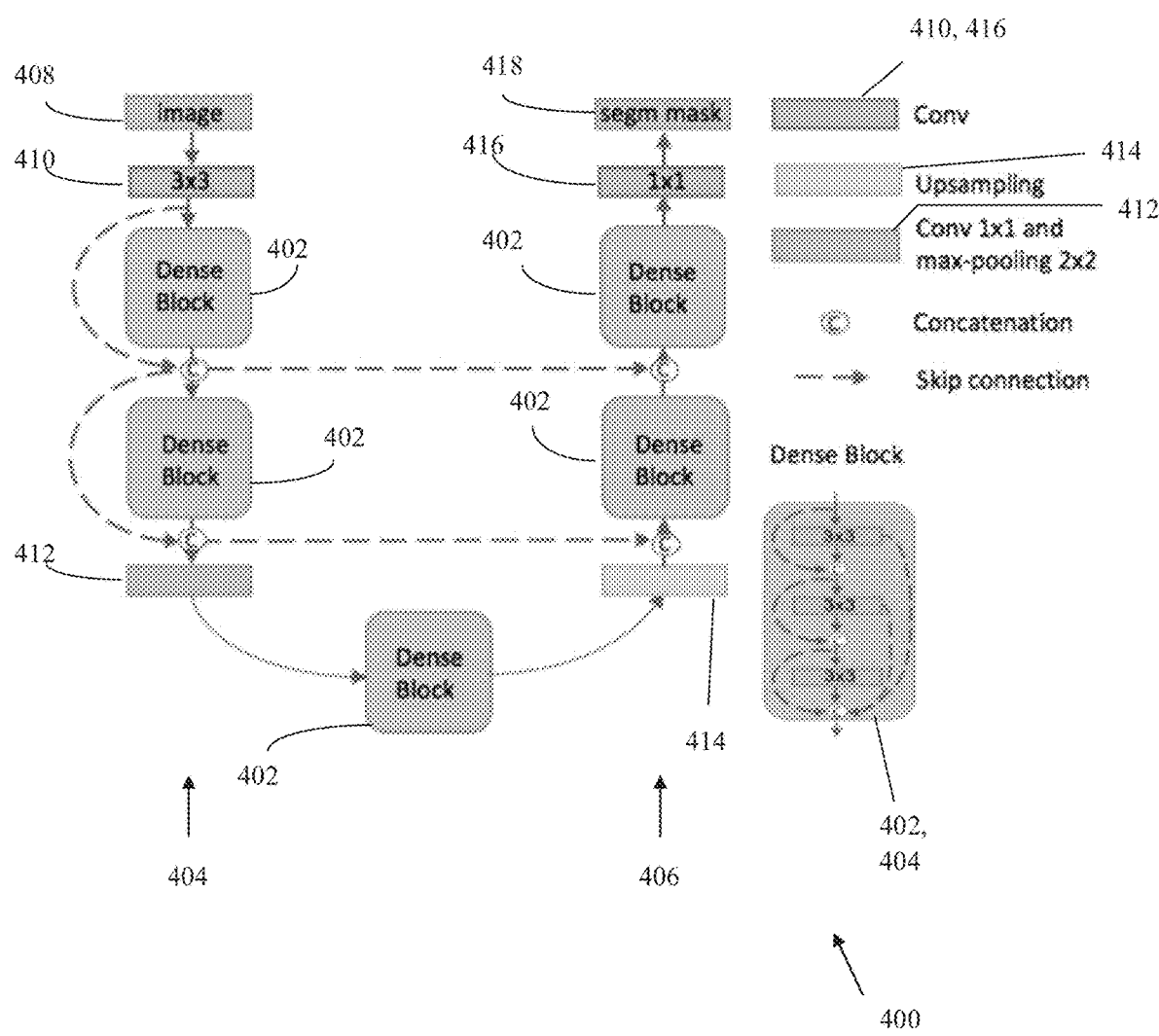
FIG. 4 is a schematic of a prior art FCN designed to process a single image, to help understand some embodiments of the present invention.

Reference is now made to FIG. 4, which is a schematic of a prior art FCN 400 designed to process a single image, to help understand some embodiments of the present invention. FCN 400 is described with reference to Jegou, S., Drozdzal, M., Vazquez, D., Romero, A., and Bengio, Y. *The one hundred layers tiramisu: Fully convolutional densenets for semantic segmentation.* arXiv:1611.09326 [cs. CV], 2016. FCN 400 is referred to by Jegou et al. as a Fully Convolutional DenseNet (FCDenseNet). The main idea underlying FCNs is extension of a contracting path, in which a sequence of pooling operators progressively reduces the size of the network, by adding successive layers where pooling operators are replaced by upsampling operators. In FCN 400, the expanding path is characterized by a large number of feature channels, allowing the network to propagate context information to higher resolution layers. In order to localize, high resolution features from the contracting path are combined with the upsampled output. A successive convolution layer can then learn to assemble a more precise output based on this information.

FCN 400 includes 2n+1 dense blocks 402 (example depicted is where n=2). Two dense blocks 402 are part of a contracting path 404, two dense blocks 402 are part of an expanding path 406, and a single dense block 402 links between the contracting and expanding path. Each dense block 402 includes $k_i$ 3×3 convolution-dropout-batch normalization-ReLU sandwich layers (shown in blow-up 404 of one denseblock 402), where i=1, . . . , 2n+1. Within each dense block 402, each 3×3 convolution layer is connected to all the following 3×3 convolutional layers via a concatenation (denoted ©) with the skip connections (denoted by arrows with broken lines).

At the beginning of contracting path 404 (i.e., that receives image 408), there is an additional 3×3 convolutional layer 410, in continuation a 1×1 convolutional layer and 2×2 max pooling with stride two 412 follows every dense block 402, and at the end of contracting path 404 a bottleneck dense block 402. FCDenseNet includes additional skip connections (shown as arrows with broken lines) from dense block 402 input to dense block output 402 in contracting path 404. Every step in the expansion (also referred to as upsampling) path 406 includes a 2×2 transposed convolution with stride twelve 414, a concatenation (represented as ©) with the correspondingly cropped feature map from the contracting path 404 and a dense block 402. At the end of expanding path 406, a 1×1 convolution 416 is applied followed by a softmax, which results in a probability map of the same dimensions as the input image (also referred to as a segmentation mask) 418. A weighted cross-entropy loss function is applied on the probability map 418. The number of filters in all 3×3 convolutional layers of dense blocks 402, except the first one layer 410 (48 filters), is the same and denoted as g (growth rate). The last 1×1 convolutional layer 416 has a number of channels that equals the number of classes and in all other 1×1 convolutional layers (including transposed convolution) the number of filters equals number of input channels.

Figure 5:
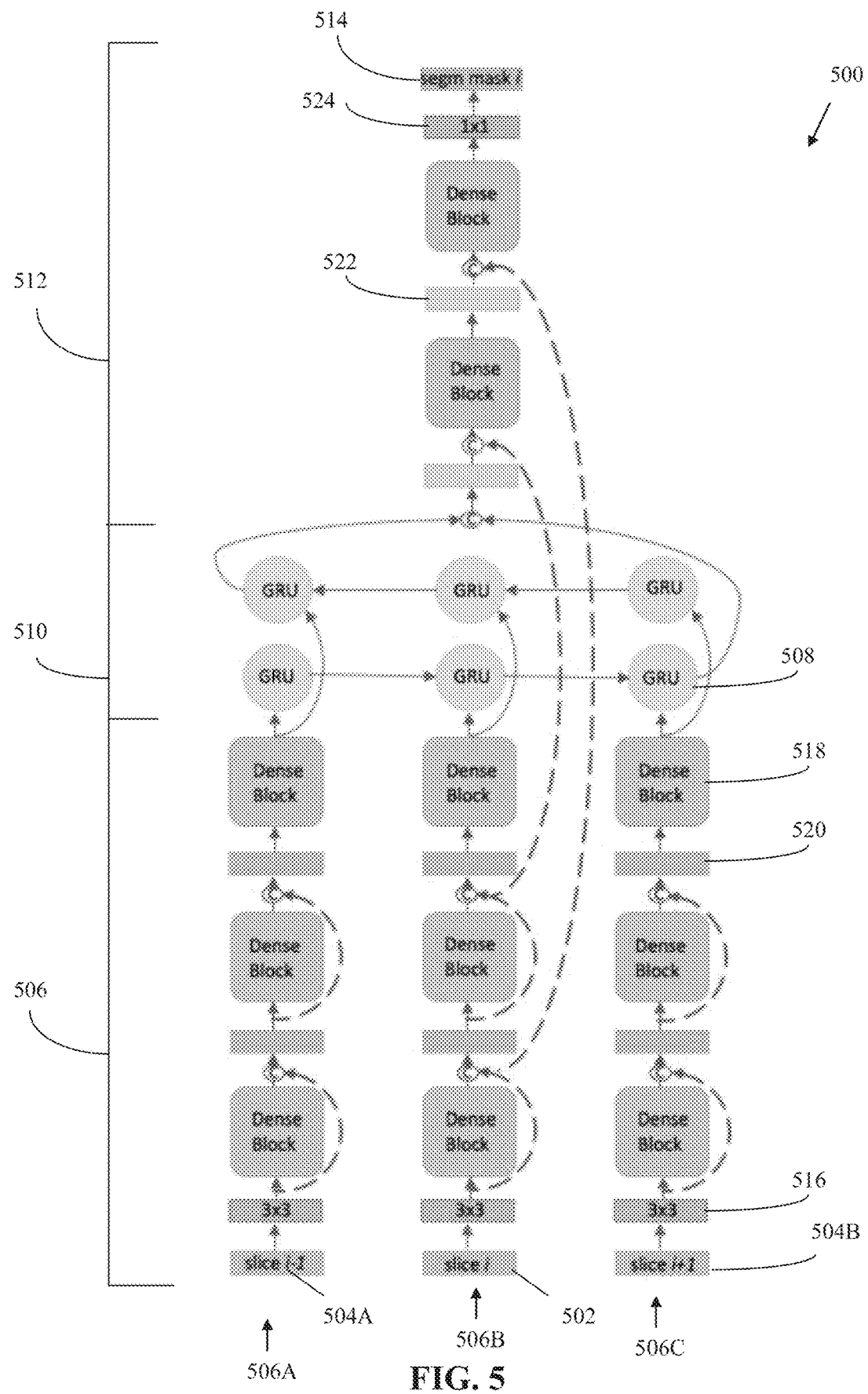
FIG. 5 is a block diagram of an exemplary architectural implementation of a multi-slice FCN, in accordance with some embodiments of the present invention.

Reference is now made to FIG. 5, which is a block diagram of an exemplary architectural implementation of a multi-slice FCN 500, in accordance with some embodiments of the present invention. Multi-slice FCN 500 receives a target slice 502 (denoted as slice i) and one or more nearest neighbor slices. The example of multi-slice FCN 500 depicted in FIG. 5 is designed to process two nearest neighbor slices 504A-B, one slice denoted i−1 located sequentially before slice i, and another slice denoted i+1 located sequentially after slice i.

The target slice 502 and each of the nearest neighbor slices 504A-B are processed by a corresponding contracting component of a set of contracting component 506 of multi-slice FCN 500 according to the order of the target slice 502 and the nearest neighbor slices 504A-B based on the sequence of 2D slices extracted from the 3D anatomical image. Contracting component 506A processes nearest neighbor slice i−1 504A, contracting component 506B processes target slice i 502, and contracting component 506C processes nearest neighbor slice i+1 504B.

It is noted that multi-slice FCN 500 may be designed to process other number of nearest neighbor slices, located before and/or after the target slice, according to the number and/or relative position of contracting components within the set of contracting components 506.

Each of the contracting components 506A-C outputs a respective feature map computed for the respective input (i.e., the target slice or one of the nearest neighbor slices). The outputs (i.e., feature maps) are fed into a respective bidirectional gated recurrent unit (GRU) (one GRU 508 marked for clarity and simplicity) of a set of GRU components 510, for example, as described by Chung, Junyoung, Gulc, ehre, C, aglar, Cho, KyungHyun, and Bengio, Yoshua. *Empirical evaluation of gated recurrent neural networks on sequence modeling*. arXiv:1412.3555 [cs.CV], year=2014. Dimensions of layers of the bidirectional GRU(s) 508 equal the dimensions of the target 2D slice and the nearest neighbor 2D slices fed into multi-slice FCN 500. The feature maps outputted by the set of sequential contracting components 506 are flattened into a single feature map that is fed into the single expanding component 512.

Outputs of a forward direction and a backward direction of the bidirectional GRU(s) 508 are concatenated (denoted ©) and reshaped into dimensions corresponding to dimensions of feature map outputs of the set of sequential contracting components 506.

Outputs of the bidirectional GRU(s) 508 are combined and processed by a single expanding component 512. Outputs of the set of sequential contracting components 506 are combined and processed by single expanding component 512.

Single expanding component 512 outputs a segmentation mask 514 for the target 2D slice i 502. Segmentation mask 514 may represent a classification of each pixel of target slice 502, as belonging to the segmented region, or not belonging to the segmented region.

Multi-slice FCN 500 includes skip connections (depicted as arrows with broken lines) between the contracting component (506B) processing the target 2D slice 502 and single expanding component 512. No skip connections are necessarily implemented between the other contracting components (506A, 506C) that process the nearest neighbor slices (504A, 504C).

3×3 convolutional layers 516 (one 3×3 layer 516 marked for simplicity and clarity) may be implemented, for example, as described with reference to layer 410 of FCN 400 of FIG. 4.

Dense blocks 518 (one dense block 518 marked for simplicity and clarity) may be implemented, for example, as described with reference to dense block 402 of FCN 400 of FIG. 4.

Down sampling layer 520 within set of downsampling components 506 (one downsampling layer 520 marked for simplicity and clarity) may be implemented, for example, as described with reference to cony 1×1 and max-pooling 2×2 layer 412 of FCN 400 of FIG. 4.

Upsampling layer 522 within expansion component 512 (one upsampling layer 522 marked for simplicity and clarity) may be implemented, for example, as described with reference to upsampling layer 414 of FCN 400 of FIG. 4.

1×1 convolutional layer 524 may be implemented, for example, as described with reference to 1×1 convolutional layer 416 of FCN 400 of FIG. 4.

Referring now back to FIG. 1, at 108, an indication of the segmented region that includes the predefined intra-body anatomical feature for the target 2D slice is provided. The indication may be represented as a mask. The target 2D slice may be adapted according to the mask, for example, by performing an operation between pixels of the 2D slice and corresponding pixels of the mask (e.g., addition, multiplication).

The indication and/or processed target 2D slice according to the indication may be presented on a display. For example, the target 2D slice may appear in black and white, and the segmentation region(s) may appear as colored pixels within the black and white image. In another example, the segmented region(s) may appear as border outlines overlaid on the target 2D slice.

Optionally, one or more scores are computed according to the indication of the segmented region that includes the predefined intra-body anatomical feature. For example, when the anatomical feature includes coronary calcification, the Agatston score may be computed. The Agatston score may be computed by multiplying the area of coronary calcification according to the segmentation region by the density in Hounsfield units of the pixels in the segmentation region. When multiple target slices of the same 3D image are analyzed, Agatston sub-scores computed for each target slice are computed and added together to arrive at the Agatston score.

Referring now back to FIG. 3, at 302, one or more samples 2D slices of one or more 3D anatomical images of multiple sample individuals are obtained. For each sample 2D slice, one or more nearest neighbor 2D slices of the 3D anatomical image are obtained.

Optionally, the sample 2D slice and the nearest neighbor 2D slice(s) of the sample individuals are raw data images extracted from the 3D anatomical image, without pre-processing.

The 3D anatomical images may be acquired for a variety of clinical indications, under a variety of image acquisition protocols. The 3D anatomical image is not necessarily acquired under optimal conditions to identify the anatomical features. For example, the 3D anatomical images may be obtained from a PACS server and/or EMR server and/or radiology server, from previously acquired images for a variety of clinical indication.

Optionally, the amount of training images required to obtain good performance by the multi-slice FCN is reduced by segmentation of the sample 2D slice.

The segmentation is designed to classify the status of presence or absence of the anatomical features (e.g., abnormalities) for each sample 2D slice. The classification of the presence or absence of the anatomical features in the sample 2D may be performed by one or more of the following methods:

Training additional classifier(s) to perform the classification on the sample 2D slice.

Use the down-sampling component of the multi-slice FCN and add a classification tag (e.g., metadata, header) that classifies the slice in parallel to the upsampling component that segments the slice and follows the slice classification to classify the slice.

It is noted that some of the pixels will be wrongly identified as associated with the anatomical feature (i.e., false positive). In order to decide whether the slice as a whole includes the anatomical feature, an aggregation method based on shape and/or location may be implemented to clean up the false positive pixels to improve the classification performance. The aggregation method may be implemented as, for example, another classifier that receives the segmentation image and pixels as input. It is noted that the ability to track back the multi-slice FCN's decisions is gained.

Thresholding the minimal number of positive pixels, in order for the respective sample slice to be considered as positive for the anatomical feature. It is noted that the threshold method may generate inaccurate results, for example, in cases in which not all pixels are equal, where some pixels are highly indicative of the anatomical feature and other pixels are irrelevant to the anatomical feature.

At 304, each sample 2D slice and one or more of the nearest neighbor 2D slices that depict the defined intra-body anatomical feature are manually segmented (e.g., annotated) by a user. The intra-body anatomical feature extends through the sample 2D slice and one or more nearest neighbor 2D slices. The manual segmentation may be performed, for example, via a graphical user interface (GUI), for example, by delineating regions of each slice that include the anatomical feature within the border of the region, and/or coloring the anatomical feature with a distinct color.

Optionally, the sample 2D slice and the nearest neighbor 2D slice(s) include regions (e.g., tissues, organs) where no annotation is performed. For example, on axial slices of a chest CT, when anatomical features are annotated within the lungs, the image portion including the heart is included (for example, rather than segmenting out the lungs and/or excluding the heart from the image).

At 306, the multi-slice FCN is trained according to the annotated sample 2D slice and the nearest neighbor 2D slice(s) (of which one or more are annotated).

The multi-slice FCN is trained end-to-end.

It is noted that multiple multi-slice FCNs may be trained, each according to a respective anatomical feature.

Optionally, a single multi class multi-slice FCN is trained to identify multiple segmentations in a target slice and nearest neighbor slices, for example, for detection of bronchiectasis, coronary calcifications, and GGO. Alternatively or additionally, multiple single class multi-slice FCNs are trained, where each multi-slice FCN identified one type of segmentation in a target slice and nearest neighbor slices, for example, one multi-slice FCN for detection of bronchiectasis, another multi-slice FCN for detection of coronary calcifications, and yet another multi-slice FCN for detection of GGO.

At 308, the trained multi-slice FCN(s) are provided. The trained statistical classifier may be locally stored by computing device 204, and/or remotely accessed and/or remotely obtained over network 210.

Various embodiments and aspects of the present invention as delineated hereinabove and as claimed in the claims section below find calculated support in the following examples.

EXAMPLES

Reference is now made to the following examples of applications of segmentation by the trained multi-slice FCN described herein, which together with the above descriptions illustrate some implementations of the systems, methods, apparatus, and/or code instructions described herein in a non limiting fashion.

Inventors performed a computational evaluation according to the systems and/or methods and/or apparatus and/or code instructions described herein, based on the features and/or system components discussed with reference to FIGS. 1-3, to evaluate segmentation of 2D axial CT slices that include an indication of bronchiectasis. As described below in additional detail, the systems and/or methods and/or apparatus and/or code instructions that implement the multi-slice FCN described herein significantly improved the accuracy and/or sensitivity and/or specificity and/or Dice score of automated segmentation of indications of bronchiectasis in axial CT slices, in comparison with other neural network architectures.

A training dataset was assembled a dataset based on 175 patients from several different who had undergone CT scans of the chest for any clinical indication. Out of the 175 patients, 134 CTs contained an indication of bronchiectasis and 46 were of healthy individuals. In CT scans with indications of bronchiectasis every axial slice with abnormal bronchi signs was manually segmented by an expert radiologist. In total 3650 slices were manually segmented. All healthy studies were verified by a radiologist not to contain bronchiectasis, although the CT scans might contain small lung nodules (diameter<3 millimeters).

The training dataset included only lung slices (on average, 98 slices per patient), which were detected using code that automatically performs lung segmentation. Non-lung regions have not been masked out.

One series was selected per patient. The dataset included bronchiectasis of all types: cylindrical, varicose and cystic. It is noted that the dataset was assembled without discrimination of studies based on the basis of data acquisition protocols, for example, inspiration/expiration imaging, and technical acquisition variations, which may result in the appearance of the lung tissue (as is usually done in a pure academic research). The data variations train a multi-slice FCN that is clinically useful for a large-scale patient screening program.

Table 1 below presents a summary of the number of CT scans and slices in the training, validation, and test datasets.

TABLE 1

| | CT scans with Bronchiectasis | | | Healthy CT scans | |
|---|---|---|---|---|---|
| | | Segmented | | | |
| Dataset | CTs | Slices | All Slices | CTs | All Slices |
| Training | 99 | 2687 | 6853 | 16 | 3053 |
| Validation | 15 | 490 | 1087 | 15 | 2468 |
| Test | 15 | 473 | 1082 | 15 | 2666 |

The Fully Convolutional DenseNet (referred to as FC-DenseNet) described with reference to FIG. 4, and the multi-slice FCN described herein were each trained according to the dataset. The implementations of the FC-DenseNet and the multi-slice FCN described herein included 56 convolutional layers. The block structure of the FC-DenseNet was {4 4 4 4 4 4 4 4 4 4 4} (with g=12), where an element in the parenthesis defines the number of layers in a block.

The accuracy, sensitivity, specificity, and dice score (denoted DSC) were computed for the segmentation results of the FC-DenseNet and the multi-slice FCN, as follows:

$$Accuracy = \frac{TP + TN}{N}$$

$$Specificity = \frac{TN}{TN + FP}$$

$$\text{Sensitivity} = \frac{TP}{TP + FN}$$

$$DSC = 2\frac{TP}{2TP + FP + FN}$$

It is noted that the Dice score is not only a measure of how many positives are found, but also penalizes for the false positives.

No preprocessing was performed on the slices. Random vertical flip and random crop of 55-95% of the original image area were performed for augmentation of the data. The cross-entropy loss function was optimized using RMSProp. The initial learning rate was set to $10^{-4}$ and was halved every 14 epochs during the training. The FC-DenseNet and the multi-slice FCN described herein where each trained for 15-40 epochs (with batch sizes of 4-10). The training took between 12 to 30 hours, depending on a model, using a dual NVIDIA TitanX GPU card. The code is based on Tensorflow.

A pixel was considered positive when its probability was higher than 0.5 and a slice was considered positive when the number of predicted positive pixels was higher than a threshold which was determined by the best accuracy received on a validation set.

Results are summarized in Table 2.

TABLE 2

| Model | # of Nearest Neighbor slices | Accuracy | Specificity | Sensitivity | Dice Score |
|---|---|---|---|---|---|
| FC-DenseNet | 0 | 90.7 | 94.6 | 63.6 | 28.4 |
| multi-slice FCN described herein | 2 | 91.2 | 94.8 | 66.4 | 37.6 |
| multi-slice FCN described herein | 4 | 91.5 | 95.7 | 62.6 | 37.7 |
| multi-slice FCN described herein | 6 | 91.8 | 95.7 | 64.9 | 38.7 |

As shown in Table 2, both the best accuracy (91.8%) and best Dice score (37.8) were achieved by the multi-slice FCN described herein with the largest amount of nearest neighbor slices (six). It is noted based on the results presented in Table 2, the greatest jump in performance is from zero to two nearest neighbor slices. The increase in accuracy and Dice score slows down between higher number of nearest neighbor slices. Therefore, adding a slice above and below the target slice contributes more new information to the network than looking at further slices. The multi-slice FCN described herein shows a 4.3% false positive rate (1-specificity), which is relatively low. It is noted that sensitivity is lower than specificity, which suggests that the multi-slice FCN described herein makes a mistake in 4.3% of cases that a slice is healthy and identifies correctly a slice with bronchiectasis in 64.9% of all cases.

Figure 6:
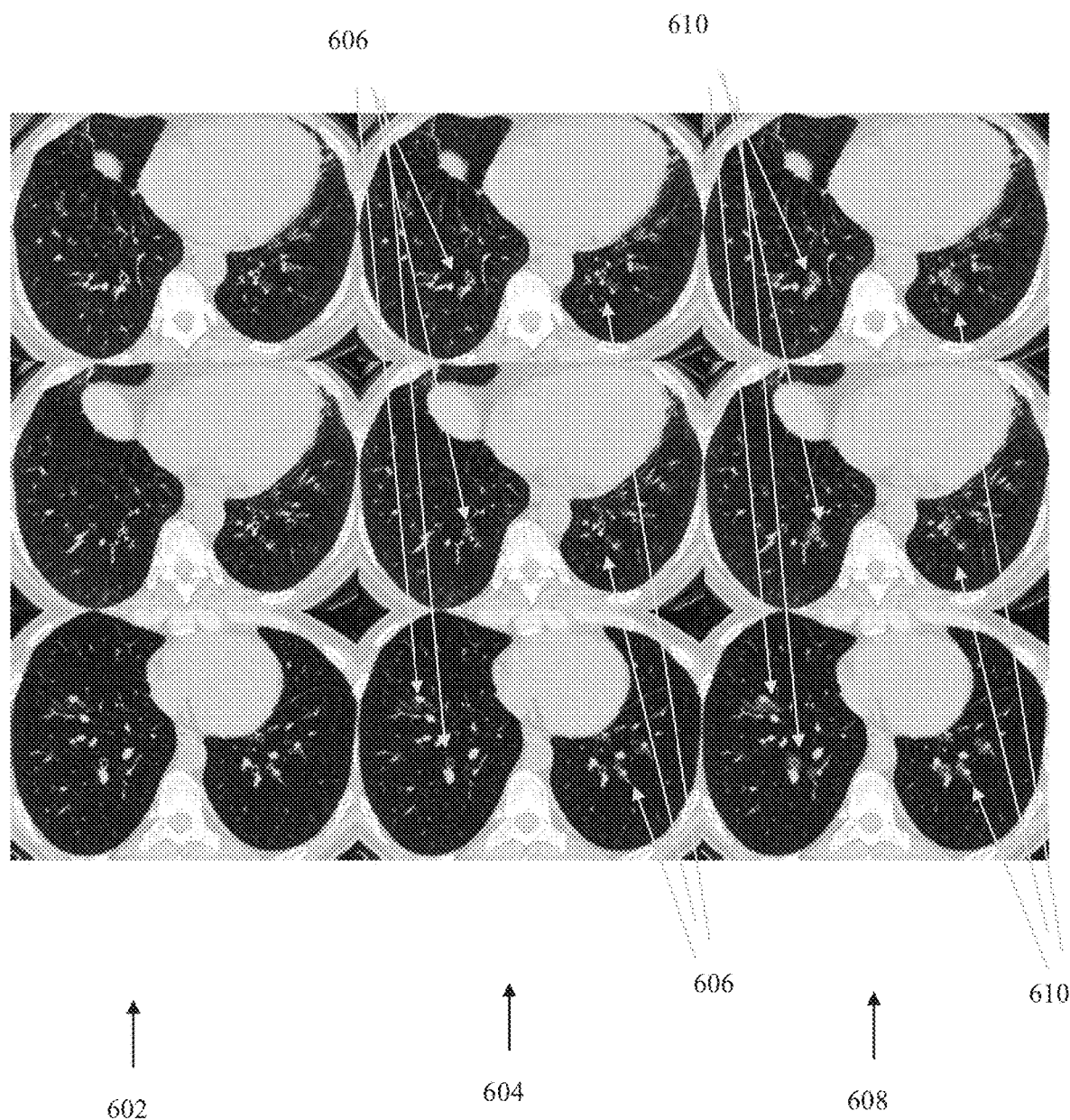
FIG. 6 includes examples of segmentation performed by the multi-slice FCN described herein, in accordance with some embodiments of the present invention.

Reference is now made to FIG. 6, which includes examples of segmentation performed by the multi-slice FCN described herein, in accordance with some embodiments of the present invention. Slices 602 include raw axial chest CT slices. Slices 604 include ground truth segmentation 606 manually performed by a radiologist. Slices 608 include automatically segmented regions 610 computed by the multi-slice FCN described herein.

A prophetic computational evaluation is now described, according to the systems and/or methods and/or apparatus and/or code instructions described herein, based on the features and/or system components discussed with reference to FIGS. 1-3, to evaluate segmentation of 2D axial CT slices that include an indication of GGO. As described below in additional detail, the systems and/or methods and/or apparatus and/or code instructions that implement the multi-slice FCN described herein are believed by inventors to significantly improved the accuracy and/or sensitivity and/or specificity and/or Dice score of automated segmentation of indications of GGO in axial CT slices, in comparison with other neural network architectures.

It is noted that the multi-slice FCN described herein as not been evaluated for segmentation of indications of GGO. The test results for segmentation of GGO by the multi-slice FCN are predictions. Results of performance by other neural networks were actually performed by the inventors, and it is predicted that the multi-slice FCN outperforms the other neural networks.

A dataset of images of 153 patients (from several Israeli hospitals) who had undergone CT scans of Chest for any clinical indication is assembled. 86 CTs included indications of GGO and 67 CTs were of healthy individuals. In CT scans with GGO indications every axial slice with ground glass signs are manually segmented by an expert radiologist (in total 4107 slices were segmented). All healthy studies are verified by a radiologist not to contain GGO, although the CT scans might contain small lung nodules (<3 mm).

The dataset includes only lung slices (on average, 120 slices per patient), which are detected using an automatic lungs segmentation code (non-lung regions have not been masked out). One series is selected per patient. The dataset includes GGOs of all types: nodule-like, medium and large, which may cover the whole lung area. It is noted that studies included in the dataset were no discriminated based on the data acquisition protocols, for example, inspiration/expiration imaging, and technical acquisition variations, which may result in the appearance of the lung tissue, as is usually done in a pure academic research. Allowing for data variations trains the multi-slice FCN for use in a large-scale patient screening program.

Table 3 below presents a summary of the number of CT scans and slices in the training, validation, and test datasets.

TABLE 3

| | CT scans with GGO | | | Healthy CT scans | |
|---|---|---|---|---|---|
| | Segmented | | | | |
| Dataset | CTs | Slices | All Slices | CTs | All Slices |
| Training | 67 | 3076 | 7279 | 13 | 2462 |
| Validation | 7 | 380 | 944 | 18 | 3059 |
| Test | 12 | 651 | 1496 | 36 | 6538 |

The multi-slice FCN described herein is predicted to outperform other neural network variations of a FCN that analyze single images, such as the U-net described with reference to Ronneberger, O., Fischer, P., Brox, T.: *U-Net: Convolutional Networks for Biomedical Image Segmentation.* MICCAI 9351, 234-241 (2015), and DenseNet described with reference to Jegou, S., Drozdzal, M., Vazquez, D., Romero, A., Bengio, Y: *The One Hundred Layers Tiramisu: Fully Convolutional DenseNets for Semantic Segmentation.* arXiv:1611.09326 [cs. CV] (2016).

Evaluations of U-net and DenseNet were actually performed. Predicted results of the multi-slice FCN described herein are prophetic.

Data is augmented by random vertical flip and random crop of 55-95% of the original image area. Cross-entropy loss function is optimized using RMSProp. The initial learning rate is set to $10^{-4}$ and it is halved every 14 epochs during the training. The networks were trained for 21-69 epochs (with batches of 10) which takes between 6 to 24 hours, depending on number of layers, using a dual NVIDIA TitanX GPU card. Code is based on Tensorflow.

U-Net and DenseNet FCN architectures of varying length were evaluated. Results of GGO detection are reported for the following networks: U-Net18 and DenseNet22 (g=12) with the block structure {2 2 2 2 2 2 2}, U-Net50 and DenseNet56 (g=12) with {4 4 4 4 4 4 4 4 4 4} and U-Net97 and DenseNet103 (g=16) with {4 5 6 7 8 9 8 7 6 5 4}, where an element in the parenthesis defines number of layers in a block.

An average Dice score was computed for each network. defined as the ratio of number of pixels (in a slice) correctly predicted as positive and sum of all ground truth positive and not correctly predicted positive pixels, averaged over all positive slices. The Dice score is not only a measure of how many positives are found, but also penalizes for the false positives. Accuracy, sensitivity and specificity are statistical measures to evaluate performance of a binary classification test, and were computed for each network. Accuracy is defined as number of all correctly identified slices divided by the total number of slices in a test set. Sensitivity is the ratio between the number of correctly identified positive slices and that of all the positive slices and specificity as the ratio between correctly identified negative slices and the total negative slices. A pixel is considered positive, if its probability is higher than 0.5 and a slice is considered positive if number of predicted positive pixels is higher than some threshold, which is defined by the best accuracy received on a validation set.

Results are summarized in Table 4.

TABLE 4

| Model | Accuracy | Specificity | Sensitivity | Dice Score |
| --- | --- | --- | --- | --- |
| U-Net18 | 94.7 | 95.9 | 81.6 | 71.0 |
| U-Net50 | 95.5 | 96.9 | 79.1 | 69.8 |
| U-Net97 | 95.1 | 96.7 | 77.1 | 72.5 |
| DenseNet22 | 96.4 | 99.3 | 63.3 | 44.6 |
| DenseNet56 | 95.4 | 96.7 | 81.5 | 55.2 |
| DenseNet103 | 96.9 | 98.3 | 80.5 | 66.8 |
| Multi-slice FCN described herein (predicted results) | >96.9 | >98.3 | >80.5 | >66.8 |

Another prophetic computational evaluation is now described, according to the systems and/or methods and/or apparatus and/or code instructions described herein, based on the features and/or system components discussed with reference to FIGS. 1-3, to evaluate segmentation of 2D axial CT slices that include an indication of coronary calcification. As described below in additional detail, the systems and/or methods and/or apparatus and/or code instructions that implement the multi-slice FCN described herein are believed by inventors to significantly improve the accuracy and/or sensitivity and/or specificity and/or Dice score of automated segmentation of indications of coronary calcification in axial CT slices, and/or significantly improve the accuracy of computing Agatston calcium score, in comparison with other neural network architectures.

It is noted that the multi-slice FCN described herein as not been evaluated for segmentation of indications of coronary calcification. The test results for segmentation of coronary calcification by the multi-slice FCN are predictions. Results of performance by other neural networks were actually performed by the inventors, and it is predicted that the multi-slice FCN outperforms the other neural networks.

From a large health provider in Israel, 848 adult non-contrast Chest CT scans with high prevalence of significant amount of CAC are collected, and used for training (512 samples) and validation (336). For testing, an additional set of 203 general indication scans are collected reflecting the distribution of age and gender in the general population. Scans with metallic artifacts or signs of deforming pathology such as cardiac surgery are excluded. Table 5 presents Agatston score distribution in the datasets.

TABLE 5

| Risk Category | Train | Validation | Test |
| --- | --- | --- | --- |
| 0 (Zero) | 15% | 29% | 32% |
| 1-10 (Minimal) | 3% | 4% | 10% |
| 11-100 (Mild) | 10% | 17% | 19% |
| 101-400 (Moderate) | 21% | 19% | 17% |
| >400 (Severe) | 51% | 31% | 21% |

For the train and validation sets, candidate CAC lesions are manually annotated by radiologists using an internally developed interactive application. Only voxels with values above the clinical standard threshold for Coronary Calcium Scoring (CCS) of 130 Hounsfield Units (HU) for example as described with reference to A S Agatston, W R Janowitz, F J Hildner, N R Zusmer, M Viamonte, and R Detrano, "*Quantification of coronary artery calcium using ultrafast computed tomography,*" American College of Cardiology, 1990 are considered. Additionally, 3 individual experts annotated the test-set data using a standard CCS module on a commercial radiology workstation (Kodak Carestream PACS). Their Agatston scores are averaged to establish ground-truth for reference.

The National Lung Screening Trial, as described with reference to National Lung Screening Trial Research Team, "*Reduced lung-cancer mortality with low-dose computed tomographic screening,*" New England Journal of Medicine, 2011 was a large-scale clinical trial aiming to compare the efficacy of CT screening and standard chest X-ray as methods of lung cancer screening, with a 6.5 years follow-up. Data from 14,365 patients is made available by the NIH for the described evaluation, of whom 452 (3.15%) had CVD related death in the follow-up, 3468 (24.14%) had reported CVD history, 1,838 (12.79%) were flagged as having significant CAC by the clinician during the study, and 8,607 (59.92%) had no documented CVD.

The images are pre-processed, by first applying a sequence of thresholding, connected components analysis and morphological operations to detect the lungs, trachea and the carina (trachea bifurcation point). Based on the location of the lungs and the carina, a set of heuristics is applied to detect a bounding box around the heart. A soft tissue window (level 40 HU, width 350 HU), which is routinely utilized for detecting CAC, is applied to the resulting volume. To provide 3D context, the volume is divided into overlapping sequences of 3 consecutive slices which are later fed into the networks being evaluated to provide pixel-wise prediction for the middle slice in the sequence. It is noted that the slices are individual analyzed by other networks, and analyzed as a set by the multi-slice FCN described herein.

The U-net architecture described with reference to O Ronneberger, P Fischer, and T Brox, "U-net: Convolutional networks for biomedical image segmentation," MICCAI, 2015 and the FC-DenseNet architecture described with reference to S Jegou, M Drozdzal, D Vazquez, A Romero, and Y Bengio, "The one hundred layers tiramisu: Fully convolutional densenets for semantic segmentation," CVPR, 2017 were actually evaluated. Predictions for performance of the multi-slice FCN described herein are prophetic. FC-DenseNet included 5 blocks on each path with 4 layers in each block and growth rate g=12, with a total of 56 convolutional layers. The U-Net architecture was based on the description by Ronneberger et al., with 23 layers with 4 blocks on each path. The U-net and FC-DenseNet architectures are trained using weighted cross-entropy loss applied on the prediction map and L2 weight regularization of 1e-4, for 40,000 iterations (roughly 13 epochs) and optimized using RMSProp. Batches of 12 randomly cropped images (up to 75% of the original size) were used. The initial learning-rate was 1e-4 which exponentially decayed with rate of 0.5 every 8,000 iterations. Both U-net and FC-DenseNet are implemented using TensorFlow and are trained for 12-14 hours on 3 NVIDIA K80s.

Model selection was based on the best performing checkpoint in terms of Agatston score prediction with regard to the validation dataset. The same model and parameters were used for all of the experiments.

After feeding the cropped axial slices through the U-Net and FC-DenseNet networks, and the set of slices (including target slice and nearest neighbor slice) a "prediction" volume is assembled where each voxel's intensity represents its probability of being a CAC voxel. 2D candidate blobs are identified on each axial slice by thresholding with 130 HU and performing connected-components analysis. Each blob is characterized by θ, which denotes a 95% percentile probability value. Each blob is classified as CAC if its θ is greater than a predefined threshold. Calculation of the final Agatston score for the whole volume is done following the clinically accepted protocol described by Agatston et al. To determine the optimal threshold, the validation set was used to exhaustively search the best threshold in terms of the smallest standard deviation of the differences between the predicted Agatston scores and the references, while limiting the search to small bias values (less than 3).

Results reported for U-Net and FC-DenseNet are based on the test dataset, which was neither used during training nor validation. Results for the multi-slice FCN described herein are prophetic. Results are reported with regards to the Agatston score computed according to the segmentation regions outputted by each neural network.

In terms of the Pearson correlation coefficient, for FC-DenseNet r=0.98 (p<0.0001) and for the multi-slice FCN r>0.98 (prophetic) between the reference and predicted Agatson score. Bland-Altman analysis shows a very small bias of 0.4 Agatston units with 95% limits of agreement of [−189.9-190.7] for FC-DenseNet, and improved results for multi-slice FCN. 3.9% of the samples lie outside the region of agreement for FC-DenseNet, and improved results for multi-slice FCN. The U-Net architecture achieves Pearson 0.97 but introduces bias of −14.5 with limits of agreement of [−252.0-222.9].

Table 6 below summarizes risk category agreement for FC-DenseNet. Agreement in cardiovascular risk categorization (I: 0, II: 1-10, III: 11-100, IV: 101-400, and V: >400) based on the Agatston score predicted by the FC-DenseNet versus reference. The linearly weighted Kappa score is 0.89, with 84.7% of the scans placed in the correct category. Another 11.3% are placed one category away, where almost 55% of the mistakes are confusing the first (zero) and second (1-10) categories, which are both difficult to differentiate and highly sensitive to small prediction mistakes. The risk category agreement is predicted to be improved for multi-slice FCN in comparison to FC-DenseNet. The U-Net architecture achieves a Kappa of 0.86 with only 81.8% of the cans placed in the correct category.

TABLE 6

| | | Reference | | | | | |
|---|---|---|---|---|---|---|---|
| | | I | II | III | IV | V | Total |
| Predicted | I | 72 | 17 | 6 | 0 | 0 | 95 |
| | II | 0 | 3 | 2 | 0 | 0 | 5 |
| | III | 1 | 0 | 27 | 1 | 1 | 30 |
| | IV | 0 | 0 | 1 | 34 | 1 | 36 |
| | V | 0 | 0 | 0 | 1 | 36 | 37 |
| | Total | 73 | 20 | 36 | 36 | 38 | 203 |

The neural networks were tested on 14,365 subjects selected from the National Lung Screening Trial (NLST), for which a median of 6.5 years follow-up was available. Some relevant insights are provided below:

1% of the patients with a predicted CCS of zero died due to CVD during the follow-up. 4% of those with scores above 400 and 6% of those with scores above 1000 died in the same interval, which suggests a correlation of the predicted CCS with the risk of cardiovascular-related death.

An exponential correlation is identified of CVD with increasing Agatston score: for risk categories I-III (0-100), 13% reported having heart attack or stroke in the past. That doubles (22%) for category IV (101-400), and doubles again (45%) for the highest category (>400).

Radiologists under-report the CAC burden: among patients with scores over 400, 32% were not reported as having significant CAC. For people with scores 100-400, 57% were not reported. This suggests the potential impact of automatic CCS quantification as described herein on regular Chest CTs.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant anatomical images will be developed and the scope of the term anatomical image is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method for automatic segmentation of a target two dimensional (2D) slice of a three dimensional (3D) anatomical image of a target patient and for computation of an indication of a defined intra-body anatomical feature, comprising:

providing the target 2D slice of the 3D anatomical image of a target individual captured by a medical imaging modality device, and at least one nearest neighbor 2D slice of the 3D anatomical image sequentially adjacent to the target 2D slice, wherein the at least one nearest neighbor 2D slice and the target 2D slice are obtained from a sequence of 2D slices extracted from the 3D anatomical image;

computing a segmentation region including a defined intra-body anatomical feature that extends spatially across the target 2D slice and the at least one nearest neighbor 2D slice, the segmentation region computed for the target 2D slice by a trained multi-slice fully convolutional neural network (multi-slice FCN) that receives the target 2D slice and the at least one nearest neighbor 2D slice as input, wherein the target 2D slice and each of the at least one nearest neighbor 2D slice are processed by a corresponding contracting component of a plurality of sequential contracting components of the multi-slice FCN according to an order of the target 2D slice and the at least one nearest neighbor 2D slice based on the sequence of 2D slices extracted from the 3D anatomical image, wherein outputs of the plurality of sequential contracting components are combined and processed by a single expanding component that outputs a segmentation mask for the target 2D slice; and providing an indication of the segmentation region including the defined intra-body anatomical feature for the target 2D slice for presentation on a display.

2. The computer implemented method of claim 1, wherein the medical imaging modality device comprises a computer tomography (CT) device, and wherein the 2D target slice and the at least one nearest neighbor 2D slice comprise 2D axial slices of the 3D anatomical image.

3. The computer implemented method of claim 1, wherein the defined intra-body anatomical feature comprises at least one arteriole indicative of bronchiectasis of at least one lung of the target patient.

4. The computer implemented method of claim 1, wherein the defined intra-body anatomical feature comprises ground glass opacity (GGO) of at least one lung of the target patient.

5. The computer implemented method of claim 1, wherein the 3D anatomical image comprises a non-cardiac non-contrast chest CT scan, and the defined intra-body anatomical feature comprises an indication of coronary calcification.

6. The computer implemented method of claim 5, further comprising computing an Agatston score by multiplying an area of coronary calcification according to the segmentation region that comprises the indication of coronary calcification by a density in Hounsfield units of pixels of the segmentation region.

7. The computer implemented method of claim 1, wherein outputs of each of the plurality of sequential contracting components comprise a respective feature map of a plurality of feature maps computed by respective sequential contracting components for respective inputs of the target 2D slice and the at least one nearest neighbor 2D slice.

8. The computer implemented method of claim 7, wherein the plurality of feature maps outputted by the plurality of sequential contracting components are flattened into a single feature map that is fed into the single expanding component.

9. The computer implemented method of claim 1, wherein outputs of the plurality of sequential contracting components are fed into a bidirectional gated recurrent unit (GRU), and a plurality of outputs of the bidirectional GRU are combined and processed by the single expanding component.

10. The computer implemented method of claim 9, wherein dimensions of layers of the bidirectional GRU equal common dimensions of the target 2D slice and the at least one nearest neighbor 2D slice.

11. The computer implemented method of claim 9, wherein outputs of a forward direction and a backward direction of the bidirectional GRU are concatenated and reshaped into dimensions corresponding to dimensions of feature map outputs of the plurality of sequential contracting components.

12. The computer implemented method of claim 1, wherein the multi-slice FCN includes a plurality of skip connections between a certain contracting component of the plurality of sequential contracting components processing the target 2D slice and the single expanding component.

13. The computer implemented method of claim 1, wherein at least one skip connection between at least one contracting component of the plurality of sequential contracting components processing the at least one nearest neighbor 2D slice and the single expanding component is absent from the multi-slice FCN.

14. The computer implemented method of claim 1, wherein the target 2D slice is located within a middle of a sequence of the at least one nearest neighbor 2D slice.

15. The computer implemented method of claim 1, wherein the at least one nearest neighbor 2D slice includes an even number of nearest neighbor 2D slices, with a first half of the even number of nearest neighbor 2D slices located sequentially prior to the target 2D slice and a second half of the even number of nearest neighbor 2D slices located sequentially after the target 2D slice.

16. A computer implemented method for training a multi-slice FCN for automatic segmentation of a three dimensional (3D) anatomical image of a target patient and for computation of an indication of a defined intra-body anatomical feature, comprising:
providing, for each respective sample individual of a plurality of sample individuals, a sample 2D slice of a 3D anatomical image of the respective sample individual captured by a medical imaging modality device, and at least one nearest neighbor 2D slice of the 3D anatomical image sequentially adjacent to the sample 2D slice, wherein the at least one nearest neighbor 2D slice and the sample 2D slice are obtained from a sequence of 2D slices extracted from the 3D anatomical image,
wherein the sample 2D slice and the at least one nearest neighbor 2D slice each include a respective manual segmentation region denoting a defined intra-body anatomical feature that extends spatially across the sample 2D slice and the at least one nearest neighbor 2D slice;
training a multi-slice FCN according to the sample 2D slice and the at least one nearest neighbor 2D slice each including the respective manual segmentation region received for each of the plurality of sample individuals,
wherein the sample 2D slice and each of the at least one nearest neighbor 2D slices for each of the plurality of sample individuals are processed by a corresponding contracting component of a plurality of sequential contracting components of the multi-slice FCN according to an order of the sample 2D slice and the at least one nearest neighbor 2D slice based on the sequence of 2D slices extracted from the 3D anatomical image of the respective sample individual,
wherein outputs of the plurality of sequential contracting components are combined and processed by a single expanding component that outputs a segmentation mask for the sample 2D slices;
and providing the trained multi-slice FCN for computing an indication of a segmented region including a predefined intra-body anatomical feature for an input of a target 2D slice and at least one nearest neighbor 2D slice of a target individual.

17. The computer implemented method of claim 16, wherein the multi-slice FCN is trained end-to-end.

18. The computer implemented method of claim 16, wherein the sample 2D slice and the at least one nearest neighbor 2D slice of the plurality of sample individuals are raw data images extracted from the 3D anatomical image, without pre-processing.

19. The computer implemented method of claim 16, wherein the sample 2D slice and the at least one nearest neighbor 2D slice of the plurality of sample individuals include regions where no manual segmentation is performed.

20. The computer implemented method of claim 16, wherein the 3D anatomical images of the plurality of sample individuals include a variation of image acquisition protocols.

21. A system for automatic segmentation of a target two dimensional (2D) slice of a three dimensional (3D) anatomical image of a target patient and for computation of an indication of a defined intra-body anatomical feature, comprising:
a non-transitory memory having stored thereon a code for execution by at least one hardware processor of a computing device, the code comprising:
code for obtaining the target 2D slice of the 3D anatomical image of a target individual captured by a medical imaging modality device, and at least one nearest neighbor 2D slice of the 3D anatomical image sequentially adjacent to the target 2D slice, wherein the at least one nearest neighbor 2D slice and the target 2D slice are obtained from a sequence of 2D slices extracted from the 3D anatomical image;
code for computing a segmentation region including a defined intra-body anatomical feature that extends spatially across the target 2D slice and the at least one nearest neighbor 2D slice, the segmentation region computed for the target 2D slice& by a trained multi-slice fully convolutional neural network (multi-slice FCN) that receives the target 2D slice and the at least one nearest neighbor 2D slice as input,
wherein the target 2D slice and each of the at least one nearest neighbor 2D slice& are processed by a corresponding contracting component of a plurality of sequential contracting components of the multi-slice FCN according to an order of the target 2D slice and the at least one nearest neighbor 2D slice based on the sequence of 2D slices extracted from the 3D anatomical image, wherein outputs of the plurality of sequential contracting components are combined and processed by a single expanding component that outputs a segmentation mask for the target 2D slice; and code for providing an indication of the segmentation region including the defined intra-body anatomical feature for the target 2D slice for presentation on a display.

* * * * *